(12) United States Patent
Heaven et al.

(10) Patent No.: US 10,280,561 B2
(45) Date of Patent: May 7, 2019

(54) MONITORING SYSTEM, CONTROL SYSTEM, AND ACTUATION ASSEMBLY OF A PAPER MACHINE

(71) Applicant: IBS of America, Chesapeake, VA (US)

(72) Inventors: Edwin Michael Gyde Heaven, North Vancouver (CA); Andrew Forester, Schoolcraft, MI (US); James Faufau, Jasper, GA (US); Jean P. Paradis, Huntersville, SC (US); Colin Bridge, North Vancouver (CA); Randy Smyth, Delta (CA); Jake Neal, Virginia Beach, VA (US)

(73) Assignee: IBS OF AMERICA, Chesapeake, VA (US)

( * ) Notice: Subject to any disclaimer, the term of this patent is extended or adjusted under 35 U.S.C. 154(b) by 0 days.

(21) Appl. No.: 15/815,910

(22) Filed: Nov. 17, 2017

(65) Prior Publication Data

US 2018/0142412 A1 May 24, 2018

Related U.S. Application Data

(60) Provisional application No. 62/425,918, filed on Nov. 23, 2016.

(51) Int. Cl.
*D21F 1/26* (2006.01)
*D21F 1/56* (2006.01)
(Continued)

(52) U.S. Cl.
CPC ............... *D21F 1/26* (2013.01); *D21F 1/486* (2013.01); *D21F 1/56* (2013.01); *D21F 1/80* (2013.01);
(Continued)

(58) Field of Classification Search
USPC ........................................................ 162/262
See application file for complete search history.

(56) References Cited

U.S. PATENT DOCUMENTS

| 1,712,632 A | 5/1929 | Peterson et al. |
| 2,305,300 A | 12/1942 | Lowe |

(Continued)

FOREIGN PATENT DOCUMENTS

| CN | 205443769 U | 8/2016 |
| DE | 102008059681 A1 | 6/2009 |

(Continued)

OTHER PUBLICATIONS

International Search Report with Written Opinion, PCT/US2017/062173, dated Mar. 7, 2018.

(Continued)

*Primary Examiner* — Mark Halpern
(74) *Attorney, Agent, or Firm* — The Dobrusin Law Firm, P.C.; Daniel P. Aleksynas

(57) ABSTRACT

A monitoring system comprising: (a) one or more sensors that monitor activity, amplitude, size, scale, duration of activity or a combination thereof of stock on a paper machine and (b) a control system in communication with the one or more sensors and one or more foil sections within the paper machine; wherein the control system measures the activity, amplitude, size, scale, duration of activity or a combination thereof of the stock and correlates the activity, amplitude, size, scale, duration of activity or a combination thereof to formation of fibers within the stock so that an angle, height, or both of the one or more foil sections are adjusted to change the activity, amplitude, size, scale, duration of activity or a combination thereof in the stock.

13 Claims, 18 Drawing Sheets

(51) Int. Cl.
*D21F 1/48* (2006.01)
*D21F 1/80* (2006.01)
*D21G 9/00* (2006.01)
*G01N 33/34* (2006.01)
*D21F 11/00* (2006.01)

(52) U.S. Cl.
CPC ............ *D21G 9/0027* (2013.01); *D21F 11/00* (2013.01); *D21G 9/0009* (2013.01); *G01N 33/346* (2013.01)

(56) References Cited

U.S. PATENT DOCUMENTS

| | | |
|---|---|---|
| 3,405,031 A | 10/1968 | Sisson |
| 3,573,159 A | 3/1971 | Sepall |
| 3,607,624 A | 9/1971 | Moody et al. |
| 3,922,190 A | 11/1975 | Cowan |
| 4,124,441 A | 11/1978 | Nykopp |
| 4,198,139 A | 4/1980 | Payne |
| 4,443,298 A | 4/1984 | Thorp |
| 4,738,751 A | 4/1988 | Newcombe |
| 4,838,996 A | 6/1989 | Kallmes |
| 4,939,929 A | 6/1990 | Ostman |
| 4,968,387 A | 11/1990 | Beran et al. |
| 5,011,573 A | 4/1991 | Niemi |
| 5,045,154 A | 9/1991 | Baluha |
| 5,080,760 A | 1/1992 | Smith et al. |
| 5,169,500 A | 12/1992 | Mejdell |
| 5,239,376 A | 8/1993 | Dittmann et al. |
| 5,269,884 A | 12/1993 | Peterson |
| 5,298,127 A | 3/1994 | Beran |
| 5,302,250 A | 4/1994 | Peterson et al. |
| 5,472,571 A | 12/1995 | Niemi |
| 5,492,601 A | 2/1996 | Ostermayer et al. |
| H1616 H | 12/1996 | Wolfe |
| 5,717,456 A | 2/1998 | Rudt et al. |
| 5,776,309 A | 7/1998 | Fraik |
| 5,830,322 A | 11/1998 | Cabrera Y Lopez Caram et al. |
| 5,922,173 A | 7/1999 | Neun et al. |
| 5,951,823 A | 9/1999 | Cabrera Y Lopez Caram et al. |
| 6,030,501 A | 2/2000 | Neun et al. |
| 6,053,040 A | 4/2000 | Callender et al. |
| 6,126,786 A | 10/2000 | White et al. |
| 6,146,502 A | 11/2000 | Marx |
| 6,362,889 B1 | 3/2002 | Mustonen |
| 6,470,598 B2 | 10/2002 | Ringer |
| 6,702,925 B2 | 3/2004 | Bricco et al. |
| 6,743,337 B1 | 6/2004 | Ischdonat |
| 6,873,353 B1 | 3/2005 | Valkonen et al. |
| 6,982,025 B2 | 1/2006 | Pitt |
| 6,988,018 B2 | 1/2006 | Eames |
| 7,169,262 B2 | 1/2007 | Bricco et al. |
| 7,318,882 B2 | 1/2008 | Niemi |
| 7,993,492 B2 | 8/2011 | Cabrera Y Lopez Caram |
| 8,236,139 B1 | 8/2012 | Reed |
| RE43,679 E | 9/2012 | VanEssen et al. |
| 8,551,293 B2 | 10/2013 | Faufau et al. |
| 8,685,209 B2 | 4/2014 | Faufau et al. |
| 8,951,389 B2 | 2/2015 | Faufau et al. |
| 9,045,859 B2 | 6/2015 | Gauss et al. |
| 2003/0116295 A1 | 6/2003 | Eames |
| 2005/0008765 A1 | 1/2005 | Karjanmaa |
| 2005/0139339 A1 | 6/2005 | Niemi |
| 2005/0150627 A1 | 7/2005 | Frawley et al. |
| 2011/0050879 A1 | 3/2011 | Shyy |
| 2011/0186254 A1 | 8/2011 | Cabrera Y Lopez Caram |
| 2013/0042987 A1 | 2/2013 | Cabrera Y Lopez Caram |
| 2015/0225897 A1 | 8/2015 | Forester et al. |
| 2016/0201262 A1* | 7/2016 | Faufau .................. D21F 1/486 162/209 |
| 2017/0067206 A1* | 3/2017 | Forester .................. D21F 1/56 |

FOREIGN PATENT DOCUMENTS

| | | |
|---|---|---|
| EP | 0837323 A2 | 10/1997 |
| EP | 1314669 B1 | 11/2002 |
| EP | 1548187 A2 | 12/2004 |
| EP | 2907918 A1 | 8/2015 |
| JP | 2002-2511536 A | 4/2002 |
| TW | M520542 U | 4/2016 |
| WO | 1999/053134 A1 | 10/1999 |
| WO | 1999/53134 A1 | 10/1999 |
| WO | 2000/045156 | 8/2000 |
| WO | 2002/046523 A1 | 6/2002 |
| WO | 2002/061203 | 8/2002 |
| WO | 2003/081219 | 10/2003 |
| WO | 2007/088456 A1 | 8/2007 |
| WO | 2008/118303 A1 | 10/2008 |
| WO | 2010/094495 | 8/2010 |

OTHER PUBLICATIONS

Co-Pending U.S. Appl. No. 15/354,179, filed Nov. 17, 2016.
Peterson, R. S., "Improving Basis Weight Uniformity with Deckle Wave Control", Tappi Journal, Technical Association of The Pulp & Paper Industry, Atlanta, US, vol. 75, No. 7, Jul. 1992, pp. 121-128.
Pruitt, M., "How fourdrinier table control affects strength and speed on linerboard—Green Bay Packaging's Morriton, AR, mill" Nov. 30, 2008, available at: http://www.risiinfo.com/magazines/November/2008/PP/PPMagNovember-How-fourdrinier-table-control-affects-strength-and-speed-on-linerboard.html, last accessed Mar. 20, 2013.
IBS Paper Performance Group, Product Brochure, 2005.
Co-Pending U.S. Appl. No. 15/075,502, filed Mar. 21, 2016.
Office Action and Search Report from the Taiwan IP Office for Application No. 107116117 dated Nov. 30, 2018.
Office Action from the Japanese Patent Office of Application No. 2018-526500 dated Jan. 11, 2019.

* cited by examiner

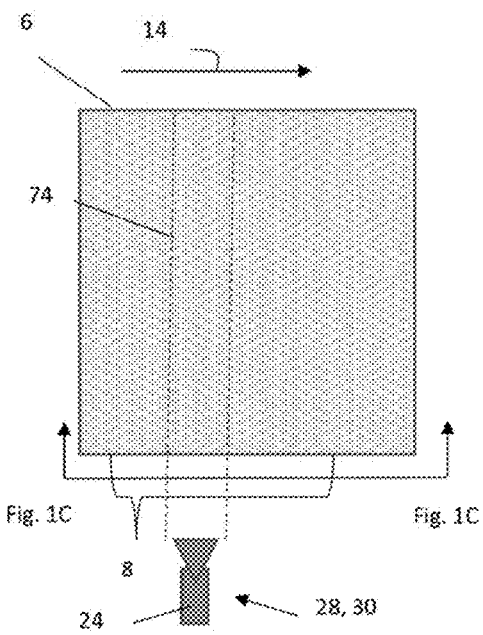
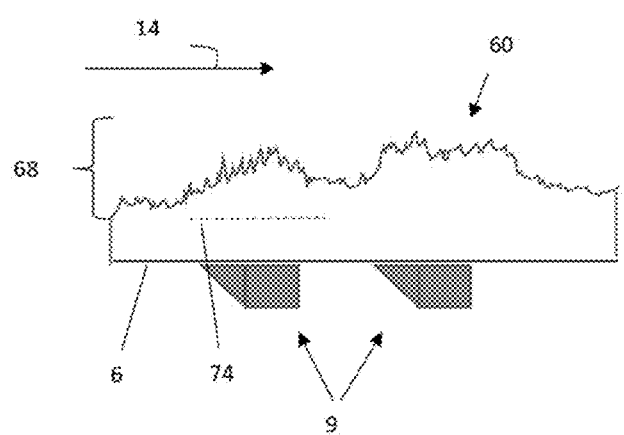
Figure 1B
Figure 1C

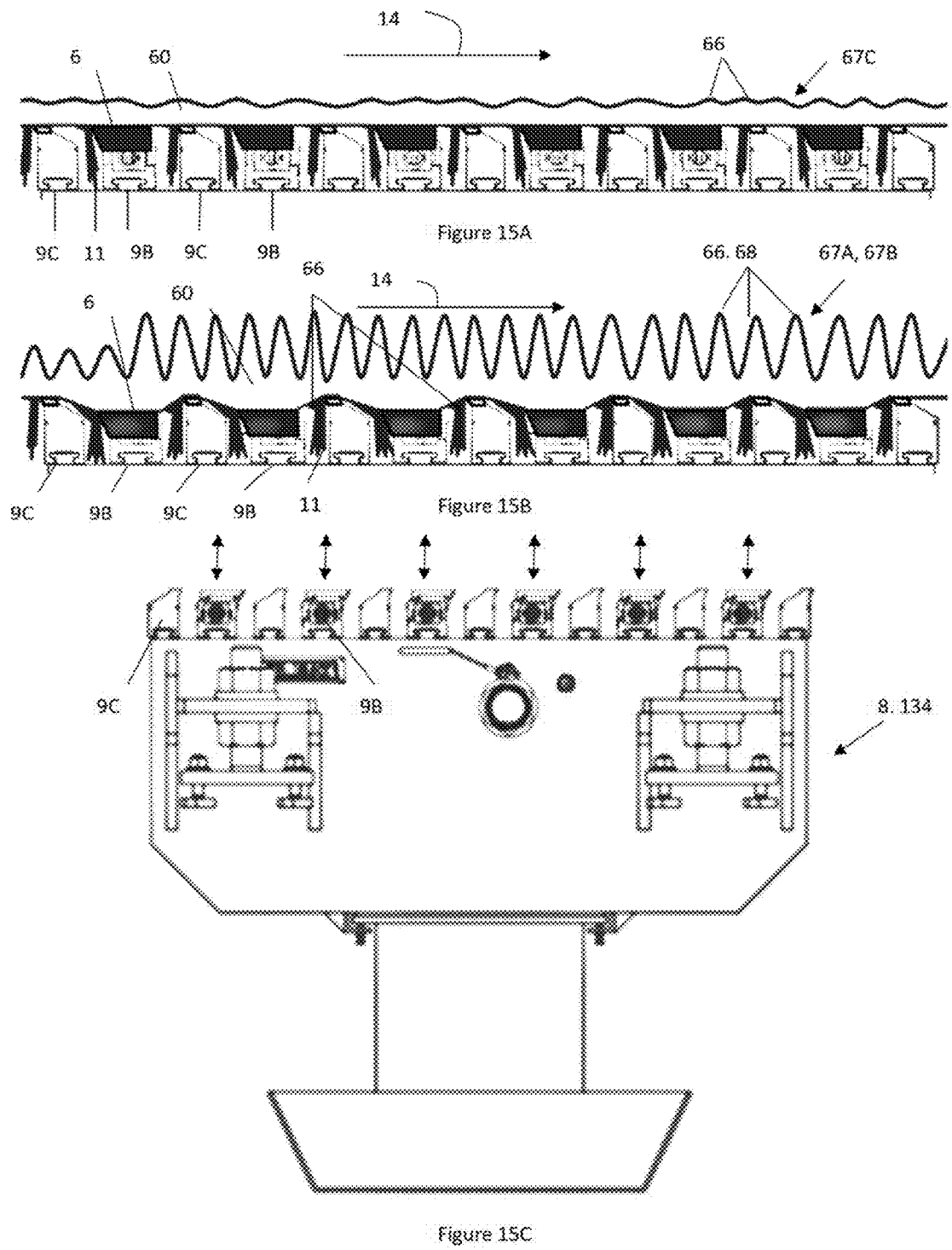

MONITORING SYSTEM, CONTROL SYSTEM, AND ACTUATION ASSEMBLY OF A PAPER MACHINE

FIELD

The present teachings relate to a monitoring system that is connected to a control system for actuating one or more components of a paper machine such as blades (e.g., foils), vacuum levels, slice opening, jet to wire ratios, activity showers, or a combination thereof on a paper machine based upon a detected condition, and a method of controlling the paper machine.

BACKGROUND

Typically, fourdrinier paper machines include a wet end with a wire that moves in a machine direction. The wire has a width (i.e., cross-machine direction) and stock is applied substantially along the entire width of the wire. A plurality of blades are located under the wire and the plurality of blades assist in removing water from the stock on the wire. The blades are typically static, however, more recently foils and blades that actuate have been added to the wet end. A deckle may be used on both edges of the wire to retain substantially all of the stock on the wire. Deckle boards are used to create an edge on a paper machine and to retain stock, water, fines, filler, or a combination thereof on the wire of the paper machine. Typically, changes to the paper machine are made by a user adjusting machine characteristics such as a slice opening or machine speed based upon dry end test results. Thus, there is a delay between testing dry end paper and making machine adjustments at the wet end of the paper machine, causing additional waste product, out of specification product, or increasing a duration of a grade change.

Examples of monitoring and adjustment devices for paper machines are disclosed in U.S. Pat. Nos. 5,239,376; 5,472,571; 5,492,601; 8,551,293; 9,045,859; International Patent Application Publication No. WO2003/081219 all of which are expressly incorporated herein by reference for all purposes. Thus, there is a need for a device that monitors activity, amplitude, scale, duration of changes, table activity, or a combination thereof. What is needed is a device that monitors and saves activity amplitude, scale, the duration of changes, or a combination thereof and at a later date resets the paper machine to duplicate the saved activity amplitude, scale, the duration of changes, table activity, or a combination thereof. What is needed is a monitoring system that monitors the wet end and allows for real time changes to be made without waiting for dry end testing data. What is needed is a monitoring system that measures an amplitude of activity and scale. What is needed is a monitoring system that is located substantially overhead of the paper machine and monitors the cross-machine direction of the paper machine as the stock travels under the monitoring system.

SUMMARY

One possible embodiment of the present teachings provide: a monitoring system comprising: (a) one or more sensors that monitor activity amplitude, scale, duration of activity or a combination thereof of stock on a paper machine and (b) a control system in communication with the one or more sensors and one or more foil sections within the paper machine; wherein the control system measures the activity, amplitude, scale, duration of activity or a combination thereof of the stock and correlates the activity, amplitude, scale, duration of activity or a combination thereof to formation of fibers within the stock so that an angle, height, or both of the one or more foil sections are adjusted to change the activity, amplitude, scale, duration of activity or a combination thereof in the stock.

The present teachings provide: (a) a control system comprising: a controller; (b) a transmitter; and (c) one or more communication devices that receive signals from a monitoring system that monitors one or more locations of a paper machine; wherein the one or more communication devices receive the signals from the monitoring system and send the signals to the controller where the controller compares an activity, amplitude, size, scale, duration of activity, or a combination thereof to an activity change; and wherein the transmitter transmits a control signal from the controller to one or more foils, blades, vacuum, slice openings, jet to wire rations, or a combination thereof of a paper machine.

The present teachings provide: a method comprising: (a) monitoring one or more regions of a paper machine to obtain current activity, current amplitude, current size, current scale, current duration of activity, or a combination thereof of the one or more regions; and (b) comparing the current activity, the current amplitude, current size, current scale, current duration of activity, or a combination thereof to a reference activity, a reference amplitude, reference size, reference scale, reference duration of activity, or a combination thereof respectively to determine a difference in activity, a difference in amplitude, a difference in size, a difference in scale, a difference in duration of activity, or a combination thereof of the one or more regions.

The present teachings provide: a monitoring system comprising: (a) one or more sensors that monitor activity of stock on a paper machine and (b) a control system in communication with the one or more sensors and one or more foil sections within the paper machine; wherein the control system measures the activity of the stock and correlates the activity to formation of fibers within the stock so that an angle, height, or both of the one or more foil sections are adjusted to change the activity of the stock.

A control system comprising: (a) a controller; (b) a transmitter; and (c) one or more communication devices that receive signals from a monitoring system that monitors one or more locations of a paper machine; wherein the one or more communication devices receive the signals from the monitoring system and send the signals to the controller where the controller compares an activity to an activity change; and wherein the transmitter transmits a control signal from the controller to one or more foils of a paper machine.

A method comprising: (a) monitoring one or more regions of a paper machine to obtain current activity of the one or more regions; and (b) comparing the current activity to a reference activity respectively to determine a difference in activity of the one or more regions.

The present teachings provide a device that monitors and saves activity, scale, amplitude, duration of changes, table activity, or a combination thereof and at a later date resets the paper machine to duplicate the saved activity, scale, amplitude, duration of changes, or a combination thereof. The present teachings provide a monitoring system that monitors the wet end and allows for real time changes to be made without waiting for dry end testing data. The present teachings provide a monitoring system that monitors an amplitude of activity and scale. The present teachings provide a monitoring system that is located substantially overhead of the paper machine and monitors the cross-machine direction of the paper machine as the stock travels under the monitoring system.

BRIEF DESCRIPTION OF THE DRAWINGS

FIG. 1B is a top view of a cross-section of the paper machine;

FIG. 1C is a side view of FIG. 1B along lines 1C-1C;

FIG. 15A illustrates a section of blades adjusted to have a low stock activity;

FIG. 15B illustrates a section of blades adjusted to have a high stock activity;

FIG. 15C is a side view of a section including both height adjustable blades and static blades;

DETAILED DESCRIPTION

Figure 1A:
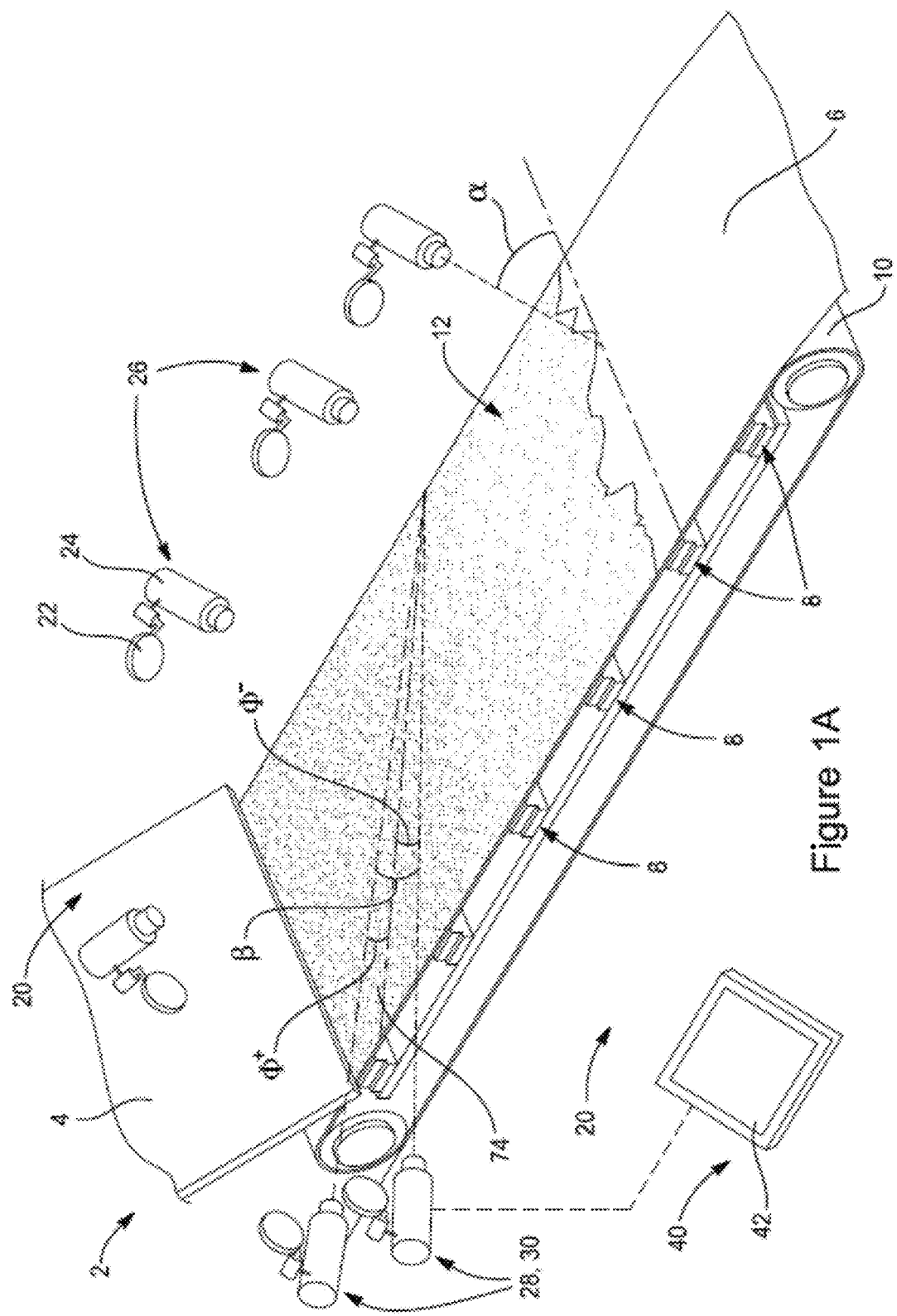
FIG. 1A is a perspective view of a wet end of a paper machine.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings are predicated upon providing an improved monitoring system, control system, method, or a combination thereof for a paper machine, and preferably a fourdrinier paper machine. The paper machine may be any paper machine where stock traveling in a machine direction may be monitored and controlled. The paper machine taught herein may be any paper machine that functions to create paper. The paper machine may be any style and/or type that forms paper. The paper machine includes a head box that applies stock in a wet end.

The head box may be gravity fed, pressurized, or both. The headbox may apply stock at a speed slower than the speed a wire in the wet end is moving (e.g., drag mode). The headbox may apply stock at a speed faster than the speed a wire in the wet end is moving (e.g., rush mode). The headbox may apply stock substantially at the same speed as the wire in the wet end is moving (e.g., square mode). The head box may function to apply stock to a wet end, above a breast roll, on foils, or a combination thereof. The head box may function to apply stock to a wire while the wire passes over a forming board or over a forming section. The head box may apply stock to the wire at a location proximate to a breast roll and a forming board. The head box may have a top portion that is movable up and down. For example, a static head of fluid may be adjusted by moving a top of the head box up or down, or the amount of stock applied to the wire may be adjusted by moving a top of the head box up or down (e.g., adjusting a slice opening. The head box may include one or more slice openings.

The slice opening may function to guide stock from the head box onto the wire. The slice opening may vary a velocity of stock traveling onto a wire, a volume of stock onto a wire, an angle of stock approaching a wire, or a combination thereof. The slice opening may be adjusted. The slice opening may have a top portion or a bottom portion that are movable. The top portion may increase a height or decrease a height of a slice opening. The top portion may pivot so as to change an angle of the stock jet while increasing a distance between the top portion and the bottom portion. The bottom portion may be movable in the machine direction. The bottom portion may change a distance between the head box and the forming board. The bottom portion, the top portion, or both may change an angle of the stock jet relative to the wire, the forming board, or both. The top portion, the bottom portion, or both may move in the machine direction (e.g., forward and backward); up and down (e.g., towards and away from the wire; pivot a portion towards or away from the wire; or a combination thereof. The slice opening may affect a contact location, contact angle, stock velocity, or a combination thereof of the stock jet relative to the wire, breast roll, forming board, forming section, or a combination thereof.

The stock jet functions to place stock on a wire while beginning to impart certain characteristics into the fibers in the stock. For example, if a stock jet is moving slower than a wire (e.g., drag) the fibers may tend to be aligned in the machine direction. In another example, if the stock jet is moving at a same speed as the wire the fibers may tend to be more randomly oriented than when the stock jet is in rush or drag. The stock jet may be substantially parallel to the wire. The stock jet may impinge into the wire. The stock jet may extend out of the slice opening at an angle of about 1 degree or more, about 3 degrees or more, about 5 degrees or more, about 7 degrees or more, or about 10 degrees or more relative to a plane parallel to the wire so that the stock jet is angled towards the wire. The stock jet may extend out of the slice opening at an angle of about 45 degrees or less, about 30 degrees or less, or about 15 degrees or less relative to a plane parallel to the wire so that the stock jet is angled towards the wire. The stock jet may first hit a bottom of the slice opening before being transferred to the wire. The stock jet may come out of the slice opening and first contact the wire above the breast roll or the forming board. The stock jet may exit the slice opening and hit the wire between the breast roll and the forming board or forming section. The angle, contact location, speed, velocity, or a combination thereof may be controlled depending on measured activity on the wire of the paper machine. Depending on the angle, speed, consistency, contact location, or a combination thereof the stock may begin to be dewatered by the wire by water being forced through the wire.

The wire may be a porous continuous belt that travels between the breast roll and the couch roll and carries stock. The wire may be flexible enough to be moved and changed by the foils within the various foil sections. The wire may be metal, plastic, a polymer, woven, non-woven, or a combination thereof. The wire may include pores so that water may be removed from the stock but solids retained. The wet end may have a wire that travels in a machine direction with stock and the stock is dewatered as the wire moves in the machine direction. Preferably, the wet end includes an endless wire that travels in a machine direction. The width of the wire may extend in the cross-machine direction. The wet end may have opposing edges that may have stock that runs along a cross-machine direction and falls off the wire. The wet end may end with a couch roll (i.e., couch roll end) that functions to wrap the wire and guide the wire in a direction opposite the machine direction so that an endless wire is formed. The couch roll may function to dewater. The couch roll may include suction. The couch roll may end the wet end. The couch roll may assist in guiding a sheet from the wet end into a press section. The stock may be sufficiently dry when the stock reaches the couch roll that the stock has paper like qualities and is self-supporting. The stock may be sufficiently self-supporting once a dry line is visible in the stock. The dry line may be monitored by a monitoring system. The wire may carry stock from the head box to a press section.

Stock as discussed herein is a slurry of fibers mixed in water and optional paper chemicals to enhance certain final paper characteristics. Stock may include fiber, fines, filers, chemicals, virgin fibers, recycled fibers, synthetic fibers, mineral fibers, glass fibers, polymer fibers, or a combination thereof. The stock preferably is at 90 percent or more, 95 percent or more, or even 99 percent or more water at the headbox (e.g., has a consistency of about 1 percent or less stock and 99 percent or more water by weight). As the stock travels in the machine direction (i.e., a direction of movement from a wet end to a dry end) the foils or blades and groups of foils (e.g., foil sections) or groups of blades (e.g., blade sections) remove the water and consistency (i.e., percentage of water in the stock) decreases. Water may continually be removed from the stock as the stock travels toward the wet end. The stock at some point will go from being a primarily liquid state to being a primarily solid state, which is referred to a dry line (i.e., a visible point on the paper machine where the tock goes from dark to light (typically at a sheet consistency of between about 8 percent to about 10 percent)).

The dry line functions to indicate that a sheet is formed and the sheet is becoming solid. The water may be removed to a point where a "dry line" is visible. The dry line is a line that forms in the cross-machine direction (i.e., a direction 90 degrees to the machine direction) where a sufficient amount of water is removed so that the stock no longer appears glossy or wet. The dry line may be substantially straight. The dry line may be staggered and the dry line may appear at edges of the paper machine before the dry line appears in a center of the paper machine. For example, the dry line may appear to have one or more fingers. The dry line may be monitored by one or more sensors. The one or more sensors may monitor a contrast from a wet side to a dry side of the dry line. The one or more sensors may monitor a width of a transition zone from a wet side to a dry side of the dry line. The one or more sensors may monitor a shape of the dry line, a length of fingers extending form the dry line, a histogram of movement of regions or fingers of the dry line, or a combination thereof. The dry line is located between the breast roll and the couch roll. The dry line may occur after a wet line (i.e., downstream in the machine direction).

The wet line may function to indicate a location on the paper machine where a sufficient amount of water is removed so that the stock no longer reflects light or has a mirrored appearance. The wet line may occur at a consistency of between about 5 percent and about 6 percent (i.e., about 5 percent solids and 95 percent water by weight). The wet line may indicate that sheet formation has occurred. The wet line may indicate that the fibers are immobilized. The wet line may occur after the stock activity line.

The stock activity line may function to indicate where turbulence, activity, or both end on the paper machine. The stock activity line may be located upstream of the wet line and the dry line. The stock activity line may be a line where a sufficient amount of water is removed so that the fibers become suspended, the stock begins to solidify, the fibers begin to lie on the wire, or a combination thereof. The stock activity line may indicate a location where formation has begun and activity may need to be reduced or eliminated. The stock activity line may indicate a consistency of about 2 percent or more, about 3 percent or more, or even about 4 percent or more. The stock activity line may indicate a consistency of about 3 percent to 4 percent. The stock activity line may occur after the breast roll, after the first section, after the second section, or after the third section but before the wet line, the dry line, or both.

The breast roll may be the first roll of the wet end (i.e., at the head box end), may assist in formation, may remove water from the stock, or a combination thereof. The breast roll may be the lead roll in a wet end. The breast roll may be located on an opposite end of the wet end as the couch roll in the machine direction. The couch roll may be a last roll on the wet end of the paper machine. The couch roll may be located between the wet end and the press sections. The wet end may function to receive stock and dewater stock. One or more forming boards, forming sections, or both may be located between the breast roll and the foil sections.

A forming section may be located downstream of the breast roll. The forming section may function to assist in receiving stock from the slice opening and to assist in configuring the stock so that fibers in the stock are oriented in a desired orienting (e.g., machine direction, cross machine direction, random). The forming section may include one or more foils, one or more forming boards, or both. The first foil of all of the foil sections may be a forming board. The forming board may be static. The forming board may be movable in the machine direction. The forming board may move so that the distance between the forming board and the head box is increased or decreased. The forming board may be height adjustable. The forming board may be angle adjustable. The forming board may be moved to increase or decrease the amount of water removed from the stock jet.

The wet end may be a portion of the paper machine where the paper has a consistency of about 15 percent or less or about 10 percent or less. The wet end may be a portion of the paper machine that is located upstream of a press section. The wet end may receive stock that is primarily water and remove the water until a sheet is formed. The wet end may have one or more and preferably a plurality of foil sections (or blade sections). For example, the wet end may have a first section, second section, third section, fourth section, or more. The wet end may remove water from stock. The wet end may impart activity into the stock so that formation of the stock is controlled, formation of a sheet of paper is controlled, the fibers are oriented or reoriented, the fibers remain suspended within water. The wet end may include one or more activity showers.

The one or more activity showers may function to introduce turbulence, activity, water, chemicals, or a combination thereof into the wet end. The one or more activity showers, may be located in or over a first section, a second section, a third section, a fourth section, or a combination thereof. The one or more activity showers may add water, spray water, or create turbulence within the stock that has been placed on the wire so that the stock may be dewatered, reoriented, maintained in solution, or a combination thereof. The one or more activity showers may break-up fibers on the wire. The one or more activity showers may spray a fluid, jet a fluid, drop a fluid, or a combination thereof into the stock or unto the wire. The activity shower may be controlled by the control system, the monitoring system, or both. The activity shower may be controlled by changing pressure of the fluid coming out of the activity shower (e.g., increasing or decreasing); changing a volume of fluid coming out of the activity shower (e.g., increasing or decreasing); changing temperature of the fluid; varying an angle of the fluid coming out of the activity shower relative to the stock; or a combination thereof. If activity is not within a predetermined parameter then the activity shower may be turned on, turned off, increased, decreased, or some condition therebetween to change the activity within the wet end. The wet end may have a plurality of sections of foils or blades.

The first section may function to begin dewatering stock as the stock exits the head box, the slice opening, the forming board, the forming board section, or a combination thereof. The first section may include static foils, height adjustable foils, angle adjustable foils, or a combination thereof. The various foils may be alternating; only static; all height adjustable foils; all angle adjustable foils; height adjustable foils and angle adjustable foils; height adjustable foils and static foils; angle adjustable foils, height adjustable foils, and static foils; or a combination thereof. Preferably, the first section is a combination of angle adjustable foils and height adjustable foils; all height adjustable foils; or all angle adjustable foils. The first section may be vacuum assisted. The first section may be free of vacuum assistance. The first section may be located directly upstream of the second section.

The second section may function to continue dewatering stock as the stock travels in the machine direction. The second section may dewater stock that is exiting the first section. The second section may include static foils, height adjustable foils, angle adjustable foils, or a combination thereof. The various foils may be alternating; only static; all height adjustable foils; all angle adjustable foils; height adjustable foils and angle adjustable foils; height adjustable foils and static foils; angle adjustable foils, height adjustable foils, and static foils; or a combination thereof. Preferably, the second section is a combination of static foils and height adjustable foils with vacuum assist. The second section may be vacuum assisted. The second section may be free of vacuum assistance. The second section may be located directly upstream of the third section.

The third section may function to continue dewatering stock as the stock travels in the machine direction. The third section may dewater stock that is exiting the second section. The third section may include static foils, height adjustable foils, angle adjustable foils, or a combination thereof. The various foils may be alternating between different types of foils; only static; all height adjustable foils; all angle adjustable foils; height adjustable foils and angle adjustable foils; height adjustable foils and static foils; angle adjustable foils, height adjustable foils, and static foils; or a combination thereof. Preferably, the third section is a combination of static foils on ends and angle adjustable foils located therebetween with the third section including vacuum assist. The third section may be vacuum assisted. The third section may be free of vacuum assistance. The third section may be followed by a fourth section, a vacuum section, steam boxes, a high vacuum section, or a combination thereof that may include blades or foils.

Blades and foils as discussed herein may be used interchangeably. The foil sections may each include one or more foils and preferably a plurality of foils. The foils may be height adjustable, angle adjustable, fixed, or a combination thereof. The foil sections may include one or more forming boards. The forming boards may be part of a forming board section. The forming board section may include height adjustable foils, angle adjustable foils, fixed foils, static foils, or a combination thereof. The foils and blades may be adjusted by any device as taught herein including devices taught in U.S. Pat. No. 8,551,293 in column no. 3, line 30 through column no. 10, and FIGS. 1-9B the teachings of which are expressly incorporated by reference herein regarding angle and height adjustable foil or blades. The foils or blades may be adjusted in angle and/or height as taught herein including devices taught in U.S. Pat. No. 9,045,859 in column 1, line 50 through Column 16, line 24 and FIGS. 1-9B the teachings of which are expressly incorporated by reference herein regarding angle and height adjustable foil blades including cam blocks, grooves, guide keys, connecting rods, thrust end blocks, pivots, foils, pneumatic, hydraulic, bending structure or a combination thereof. The wet end includes edges in a cross-machine direction (i.e., a direction that is perpendicular to a machine direction). The plurality of foils may be broken into one or more groups of foils and preferably a plurality of groups of foils that extend in the machine direction. The groups of foils may be all height adjustable, all angle adjustable, all static, or a combination thereof. The groups of foils may include both height adjustable foils and angle adjustable foils; both static and height adjustable, both static and angle adjustable; height adjustable foils, angle adjustable foils, and static adjustable foils; or a combination thereof. The types of blades may be alternating (e.g., static blades and height adjustable blades; static and angle adjustable blades; height adjustable blades and angle adjustable blades; or a combination thereof). The static blades may be located at a beginning and an end and angle adjustable or height adjustable blades may be located therebetween. The paper machine may include two or more groups of foils, three or more groups of foils, four or more groups of foils, or five or more groups of foils. Each group of foils may include two or more foils, four or more foils, six or more foils, or even ten or more foils. A first set of foils may include a forming board and then a set of foils. The types of foils (e.g., static, angle adjustable, height adjustable) may be grouped in any order. For example, the group of foils may include two angle adjustable foils then one static foil and the three height adjustable foils. Each foil may be a different type in an alternating fashion. For example, a static foil then height adjustable in a repeating pattern. The height adjustable foils may move a distance from a wire (e.g., out of contact with the wire). The height adjustable foils may move towards or away from the wire. The height adjustable foils may from away from the foil about ±1 mm or more, about ±2 mm or more, about ±3 mm or more, about ±4 mm or more, about ±5 mm or more, or about ±6 mm or more (e.g., when the foil moves towards the wire it is positive (or up) and when the foil moves away from the wire it is negative (or down)). When the height adjustable blades are in contact with the wire and the wire is not deflected then the height adjustable blades are at 0 mm. The angle adjustable blades may be adjustable in an angle from about ±1° or more, about ±2° or more, about ±3° or more, or about ±4° or more (e.g., when a tip of the blade is rotated into the wire (i.e, up pressing into the wire) the angle is positive and when the tip of the blade is rotated away from the wire (i.e., down moving away from the wire) the angle is negative, and when the tip is parallel to the wire the angle is 0°). The height adjustable foils may create vacuum on the wire that pulls the wire negative. The height adjustable foils may have a "v" shape and the valley of the "v" may assist in pulling the wire below 0° so that stock activity is created. The blades may be adjusted based upon one or more monitored conditions of a monitoring system. Preferably, a monitoring system monitors the stock at one or more locations between the headbox and the dry line or a press section.

The monitoring system may function to monitor activity, amplitude, size, scale, duration of activity, or a combination thereof of stock on a paper machine and preferably stock in the wet end of a paper machine. The monitoring system may monitor in the cross-machine direction, the machine direction, or a combination of both. The monitoring system may monitor activity, amplitude, size, scale, duration of activity, or a combination thereof in a cross-machine direction, a machine direction, or a combination of both. The monitoring system may measure stock activity, amplitude, size, scale, duration of activity, or a combination thereof (hereinafter all will be referred to as stock movement). The monitoring system may monitor stock activity, analyze stock activity, relay information regarding stock activity to a control system, or a combination thereof in real time. The monitoring system may monitor the amount of water removed by one or more of the foils; the forming board; the impingement angle between the stock jet and the wire, the forming board, or both; each stock section; or a combination thereof. The monitoring system may monitor the cut through near the head box. The monitoring system may be located at, alongside, perpendicular to, or a combination thereof a cut through on the paper machine. The cut through may be the area between the slice opening and the forming board, between the head box and the forming board, between the breast roll and the forming board, or a combination thereof. The monitoring system may monitor the width of the water being removed. The monitoring system may monitor the impingement angle between the stock jet and the forming board. The monitoring system may monitor the amount of water removed by adjusting a gap between the forming board and the head box, an angle of one or more blades, a height of one or more blades, or a combination thereof. The monitoring system may monitor the location of the bottom portion of the head box relative to the breast roll, the forming board, or both. The monitoring system may include one or more lights, one or more sensors, one or more level devices, or a combination thereof. The monitoring system may monitor the activity line, the stock activity line, a wet line, dry line, or a combination thereof. Preferably, the monitoring system includes a plurality of sensors that monitor the wet end of the paper machine.

The one or more sensors function to monitor the stock activity (i.e., movement). The one or more sensors may function to send signals to a control system so that the control system controls the stock movement. The one or more sensors function to monitor and assist in controlling stock movement (i.e., activity) in real time so that final paper quality may be changed without waiting for testing results from a dry end of a paper machine. The one or more sensors may assist in making adjustments during a grade change, normal running, or both. The one or more sensors may monitor a temperature of the stock. The one or more sensors may monitor a first side and a second side of the stock activity line, the wet line, the dry line, or a combination thereof. The one or more sensors may monitor a temperature profile, a humidity profile, a dryness profile, or a combination thereof. The one or more sensors may monitor the stock jet. The one or more sensors may monitor jet impingement of the stock jet relative to the slice opening, the wire, the forming board, the forming board section, or a combination thereof. The one or more sensors may monitor a location proximate to a steam box. The one or more sensors may monitor for streaks, temperature profile, dryness profile, or a combination thereof. The sensors may monitor stock movement and correlate the stock movement to a previous run and then provide signals to the control system to adjust the paper machine to match the activity (e.g., stock movement) of the previous run. The sensors may be a camera that takes still images, moving images, or both. The sensors may use ultrasound, infrared, CMOS sensor, charge-coupled device, matrix camera, area scan camera, line scan camera, microwave, a temperature sensor, nuclear, capacitance, pressure, vacuum, distance, suspension height, or a combination thereof. The one or more sensors may be a plurality of sensors or a multitude of sensors. All of the sensors may be the same type of sensor. Different types of sensors may be used together. For example, one sensor may be an infrared sensor and another sensor may be a CMOS sensor. The one or more sensors may be a color sensor. The one or more sensors may be monochrome sensor. The one or more sensors may monitor a dry line without use of cameras (i.e., dry line monitoring may be done without lights). The one or more sensors may be one or more sensors, two or more sensors, four or more sensors, six or more sensors, or even ten or more sensors. Each of the sensors may produce images that have a plurality of pixels. Each of the sensors may produce pixels that may be categorized. The pixels of the sensors may be categorized based upon a primary activity, secondary activity, tertiary activity, or more activities (e.g., 4 groups, 5 groups, 6 groups, or more). The groups of activity may be selected based upon one or more predetermined activity settings. The groups of activities may be compared to one or more threshold activities. The one or more threshold activities may separate the activities into a primary, secondary, tertiary, etc. . . . The primary activity, secondary activity, and tertiary activity may be measured by one or more sensors. The one or more sensors may include an air purge. The one or more sensors may include a cleaning mechanism. The one or more sensors may include a self-cleaning lens. The one or more sensors may include a wipeable lens. For example, the wipeable lens may be a self-wiping lens that upon a pre-determined amount of build-up moves so that the debris is removed from the lens. The lens may move longitudinally or radially so that a cleaned lens is moved in front of the camera. The one or more sensors may include both a cleaning mechanism and an air purge. The one or more sensors may remove vapor, fluids, steam, debris, stock, or a combination thereof. The one or more sensors may be in a location so that the sensors are a high angle sensor, a low angle sensor, a movable sensor, or a combination thereof.

The one or more movable sensors may be located above the wet end and the one or more movable sensors may move in the machine direction, the cross-machine direction, or a direction therebetween. The movable sensors may function to travel with a location on a wire. The movable sensors may travel with an area of stock. For example, the sensor may match the speed of the wire and take readings of the changes occurring to a location on the wire to determine the impact of each foil, section, or both on activity. The movable sensors may move along the stock activity line, the wet line, the dry line, or a combination thereof. The movable sensors may be connected on a frame, a wire, may be a drone, may be free of connection with any devices, may be suspended from a ceiling, may be suspended over the head box and movable along the head box, or a combination thereof. The movable sensors may zoom in, zoom out, or both. The movable sensors may be movable with a light so that an area of interest is illuminated while the movable sensor moves. The movable sensors may move diagonally. For example, the movable sensor may move in the machine direction as the movable sensor scans in the cross-machine direction so that the movable sensor measures in a straight line across the wire. The movable sensors may be a plurality of sensors. The movable sensors may be a camera, a thermal camera, a temperature sensor, or a combination thereof. There may be multiple movable sensors that move over the wet end to allow a user to monitor one or more locations of the wet end simultaneously. The movable sensors may be wired, wireless, use Bluetooth, use wifi, use radio waves, or a combination thereof. The movable sensors may be in communication with other sensors and may move to a location of interest based upon measurements taken by other sensors. The movable sensors and other sensors may be in communication with the control system and the control system may control where the movable sensor senses based upon feedback detected by the sensors (e.g., the high angle sensors, the low angle sensors, or both).

The one or more high angle sensors may function to be located above the wet end and look substantially down at the wet end to monitor the wet end of the paper machine. The high angle sensors may be located substantially overhead of the wet end. The high angle sensors may be orthogonal to the wire, the wet end, or both. The one or more high angle sensors may monitor a stock activity line, a wet line, a dry line, or a combination thereof. A plurality of high angle sensors may be located in the cross-machine direction across the paper machine. The high angle sensors may each monitor a portion of a width (i.e., cross-machine direction) of the paper machine. The high angle sensors may monitor overlapping regions. The high angle sensors may be located about 90 degrees or less, about 75 degrees or less, about 60 degrees or less, or about 45 degrees or more with the wet end, wire, foil sections, or a combination thereof. The high angle sensors may monitor the stock movement. Preferably, the high angle sensors monitor activity, size, scale, or amplitude of the stock. The high angle sensors may work in conjunction with or separately from the one or more low angle sensors.

The one or more low angle sensors may function to measure stock movement. The one or more low angle sensors preferably monitor stock amplitude and/or stock activity. The one or more low angle sensors may be substantially coplanar with the wire, the foils, the wet end, or a combination thereof. The one or more low angle sensors may be angled parallel to the cross-machine direction, perpendicular to the machine direction, or both. The one or more low angle sensors may be located a sufficient height above a deckle board to monitor stock movement on the wire, the foils, the wet end, or a combination thereof. The one or more low angle sensors may have an angle of about 0 degrees or more, about 5 degrees or more, about 15 degrees or more, about 25 degrees or more, or about 45 degrees or less with the wire, the foils, the wet end, or a combination thereof. The one or more sensors (e.g., high angle, moving, low angle, or a combination thereof) may monitor the amount of activity of the stock within a given region. For example, the sensors may count the total number of peaks (i.e., spouts that extend from the wire, which are shown in the figures as light spots or stock jumping up from the wire) formed in the stock that extend above a predetermined point (e.g., a level device or activity line). The sensor may monitor the amount of the fluid (e.g., water) being removed by each foil. For example, if one foil is removing too much fluid then the stock activity may be reduced and the fibers froze in place. In another example, if enough fluid is not removed from a foil or group of foils then a sufficient dryness may not be achieved. The one or more low angle sensors may monitor each foil or foil section so that substantially the same out of fluid is removed by each foil or foil section. The one or more low angle sensors may monitor the amplitude of the stock. For example, the low angle sensors measure a height the stock is agitated above the wire, the foils, a level device, an activity line, or a combination thereof.

The one or more level devices may function to create one or more activity lines for comparison. The level devices may create a primary activity line, a secondary activity line, a tertiary activity line, or a combination thereof. The one or more level devices may function to create an activity line to determine an amplitude, size, scale, duration, activity, or a combination thereof of the stock. The activity line may indicate an area that is being monitored (e.g., a monitoring region). The one or more level devices may function to assist in categorizing the type of activity and/or amplitude of the stock. The level device may create a physical activity line or activity plane above the paper machine that is visible by the sensors so that the sensors can determine if the activity, amplitude, size, scale, duration, or a combination thereof is above a set point, predetermined amount, calculated amount, or a combination thereof. Preferably, the one or more level devices create a computer generated activity line. For example, when an image is captured the monitoring system adds the activity line into the image for comparison. The activity line may be an invisible line that stock may be compared to in order to categorize activity in a monitoring region. The controller may add an activity line, level device, or both into the measured signal so that the stock activity can be characterized. The activity line and the level device may be aided by one or more lights in monitoring the stock movement.

The one or more lights may function to illuminate the stock movement so that the stock movement can be measured. The one or more lights may be part of the monitoring system. The one or more lights may freeze the stock so that the stock activity is visible. For example, the lights may be a strobe light. The lights may be connected to a monitoring system that may control the frequency of the lights turning on and off, the strobing of the lights, or both. The one or more lights may be connected to each of the sensors. Preferably, the monitoring system includes a plurality of sensors. Some sensors may be free of lights. The one or more lights may be a bank of lights. The one or more lights may be located with each sensor and the lights and sensors may cooperate together. The lights may work with any of the sensors. The one or more lights may be a bank of lights. One or more lights or a plurality of lights may be aligned along the wet end of the paper machine. The one or more lights may assist the monitoring system so that the monitoring system may generate and send signals to the control system.

The control system may function to change or adjust one or more paper machine settings. The control system may be connected to a monitoring system taught herein. The control system may vary the speed of the wire, angle of the foils, height of the foils, speed of stock coming out of the head box, stock jet angle, amount of suction being applied to one or more sections, vacuum levels, slice opening, stock jet speed, wire speed, jet to wire ratios, temperature of the stock, head box consistency, or a combination thereof. The one control system may be an automatic control system, a manual control system, or both. The one or more control systems may adjust an activity line, a stock activity line, or both. The one or more control systems may move a movable sensor. The one or more control systems may communicate between two or more sensors; a sensor and a light; a level device and a sensor; an activity line and a sensor or a controller; or a combination thereof. The control system may include one or more processors, one or more microprocessors, or both that analyze a plurality of images taken by the sensors and correlate the sensors to one or more dry end tests so that wet end changes may be made to effect one or more dry end tests. The control system may monitor in real time.

The control system may be a closed loop control system. The control system may adjust the paper machine for changes in furnish, ambient temperature, freeness, or a combination thereof. The control system may calculate positions of the components of the paper machine based upon measurements form the monitoring system, input measurements from operators, upstream monitoring equipment, or a combination thereof. The control system may adjust for ambient lighting conditions. For example, if it is night then the control system may measure the activity differently than if it is day outside. The lights may flood the monitoring region so that the time of day and ambient light do not affect the measurements. The control system may be part of a distributed control system (DCS). The control system may be part of the monitoring system. The control system may be in communication with one or more controllers.

The one or more controllers may be in communication with one or more components such as the head box, foils, groups of foils, wire, suction boxes, couch roll, breast roll, dilution controllers, angle adjustable foils, height adjustable foils, steam boxes, temperature control devices, or a combination thereof. The one or more controllers may be manually controlled, automatically controlled, or both. Each component (e.g., sensor, foil, foil motor, head box motor, slice opening, steam box, activity shower) may include a controller so that each component may be controlled independently or individually without reference to other components. The controllers may be remotely controlled (e.g., by a DCS, remote, or tablet). The controllers may be controlled by a wire. The controllers may be wirelessly controlled. The controllers may be locally controlled (e.g., a user standing by the paper machine manually actuating the controller or pressing a button). The controller may be controlled based upon stock activity, amplitude, size, scale, duration of activity, or a combination thereof. The controller may be a proportional controller, integral controller derivative controller, Proportional Integral Derivative controller, or a combination thereof.

The stock activity may be the number of spouts in a given region (e.g., a monitoring region). The activity may be a measured amount of spouts that extend above an activity line (e.g., amplitude). The activity may be counted. The activity may be based on an average amplitude of the spouts, a quantity of spouts in a monitored region, scale of the spouts, duration of the spouts, or a combination thereof. The activity line may be a predetermined line that may be determined based upon correlation with dry end measurements. The activity line may be a primary activity line and a secondary activity line. Activity that extends above the primary activity line may be primary activity and activity that extends above the secondary activity line may be secondary activity. Thus, the activity may be categorized based on activity relative to the activity line. The activity may be any region in the stock that is not substantially flat or created by waves. The activity may be individual stock interruptions that spout above the surrounding stock. The activity measurement may be the number of spouts within a given monitoring region. The activity measurement may be a measurement of the number of spouts in a monitoring region above an activity line.

The amplitude of stock may be a spout of stock with a height above an activity line, above a predetermined point, or both. The amplitude may any spout that extends above the surrounding stock. The spouts may be graphically represented by peaks that extend upward and taper to a peak. The stock amplitude may be categorized relative to a height of the wire, the surrounding stock, one or more activity lines, or a combination thereof. The amplitude may be the height of the spouts. The amplitude may represent an amount of activity input into the stock by the foils, the stock jet, or both. The amplitude may be divided into primary activity, secondary activity, tertiary activity, or a combination thereof. The stock activity may be monitored for amplitude, size, duration, or a combination thereof.

The size of the spouts may be a cross-sectional thickness of the spout at a predetermined location. The size of the spouts may be measured at the activity line, before the activity line, between the activity line and the head box; or a combination thereof. The size of the spouts may vary over the height of the spouts. The size of the spouts may vary as the spouts are measured in the machine direction. The spouts may decrease in size as the spouts are measured in the machine direction. For example, the spouts in the first section may be larger than the spouts in the second section. The activity line (e.g., primary activity line, secondary activity line, tertiary activity line) may vary along the machine direction. For example, as the consistency increases, due to dewatering, the size, amplitude, total activity, or a combination thereof may decrease such that the activity line may be calibrated at each section to accommodate for the increase in the consistency (e.g., more fibers by weight). The size of the spouts and the amplitude of the spouts may be directly proportional. The size of the spouts and the amplitude of the spouts may be conversely proportional.

The duration of activity may be the distance the spouts are formed after a foil or the duration spouts are created after a foil is adjusted. The duration of activity may be measured in the machine direction. The activity line may be a line that separates upstream of the activity line from downstream of the activity line so that activity before the line and the activity after the line can be measured determine the amount of activity that lasts a duration beyond the activity line. The duration of activity may be measured in seconds after a foil change. The duration, amplitude, stock activity, size, scale, or a combination thereof may be measured in a monitoring region.

The scale may be the distance between spouts, a cross-sectional thickness (e.g., diameter) of the spouts, or both. The scale may be measured in sections across the paper machine. The scale may correlate to the density of the activity. The scale or density may be directly proportional. The scale may be a number of spouts within a given area (e.g., density). The activity line may create a perimeter around a region of stock so that the activity within the region may be measured. The scale may be measured in a primary activity, a secondary activity, a tertiary activity, or a combination thereof depending upon the categorization of the activity.

The primary activity may function to indicate an amount of activity that exceeds a threshold amount of activity. The primary activity may be any activity that is over a threshold activity (e.g., over a primary activity line). The threshold activity may be amplitude, size, scale, duration, amount, height, or a combination thereof. Primary activity may indicate that the stock will achieve the desired dry end testing characteristics. The primary activity at each section may be about 20 percent or more, about 30 percent or more, about 40 percent or more, about 50 percent or more. The primary activity at each section may be about 90 percent or less, about 80 percent or less, or about 70 percent or less. The primary activity may be measured by establishing a primary activity line and a secondary activity line. Any activity over the primary activity line may be considered primary activity, any activity between the primary activity line and the secondary activity line may be secondary activity, and any activity below the secondary activity line may be tertiary activity line. More or less activity lines may be established depending upon desired levels of activity. The activity lines may be based upon amplitude of the stock. For example, a height of the droplets of stock over the wire may be measured and the number of peaks over the primary activity line may establish the primary activity. The number of peaks that fall between the primary activity line and the secondary activity line may establish the secondary activity, and the remaining peaks may establish the tertiary activity. A total activity may be calculated by adding the primary activity, secondary activity, and tertiary activity together so that a percentage of each may be calculated. The primary activity may decrease from a first section to a second section, a second section to a third section, or a third section to a fourth section. The activity lines may be adjusted to account for less activity as the paper sheet becomes drier. An amount of primary activity may be the lowest as the wire travels from the head box towards the press section. The primary activity at the stock activity line may drop to about 10 percent or less, about 5 percent or less, or about 0 percent. The primary activity may decrease from foil section to foil section. The primary activity in a first section (i.e., the section closest to the head box) may be between about 60 percent and 30 percent, between about 55 percent and about 35 percent activity, preferably between about 50 percent and about 40 percent of the total activity (i.e., about 42 percent of the total activity). The primary activity my lower from section to section. The primary activity may decrease by about 5 percent or more, about 10 percent or more, or about 15 percent or more from section to section. The primary activity may decrease by about 30 percent or less, about 25 percent or less, or about 20 percent or less. The primary activity may have a greatest decrease from the first foil section to the second foil section. For example, from a first foil section to a second foils section the primary activity may decrease by about 20 percent of the total activity, and from the second foil section to the second foil section the primary activity may decrease by about 15 percent of the total activity. The amount of primary activity may be varied from grade to grade. The primary activity may be varied by changing a primary activity line. The primary activity line may be determined by a percentage of a peak height. For example, if a peak height is 3 mm then the primary activity line may be set at 75 percent of a peak height (i.e., 2.25 mm). The peak height may be about 50 percent or more, about 60 percent or more, about 70 percent or more, about 75 percent or more, or about 80 percent or more of a peak height (e.g., amplitude) of the activity. The primary activity may change to secondary activity as measurements are taken in the machine direction. For example, in the first section the primary activity may be about 41 percent and the secondary activity may be about 3 percent and then in the second section the primary activity may be about 22 percent and the secondary activity may be about 4 percent.

The secondary activity may be activity that greater than tertiary activity but not as great as primary activity. The secondary activity may indicate activity in a foil section, but the activity may be below a threshold amount or measurement. The secondary activity may indicate that activity is being imparted into a foil section, but that an amount of activity is not sufficient to generate primary activity or that a consistency has reached a level such that primary activity is limited. The secondary activity may be changed to primary activity by adjusting one or more settings. The secondary activity may be changed to primary activity by changing height of one or more height adjustable foils, changing angle of one or more angle adjustable foils, changing height of a plurality of height adjustable foils, changing angle of a plurality of angle adjustable foils, changing steam boxes, adjusting vacuum, adjusting formation showers, or a combination thereof. The secondary activity may be increased or decreased by increasing or decreasing an amount of vacuum applied to the foil sections. The secondary activity may be varied by adjusting a slice opening, stock jet, speed of the wire, or a combination thereof. The secondary activity may be a measurement of an amplitude of the stock. For example, if 1000 peaks are measured in a monitored region then a number is counted that fall between a primary activity line and a secondary activity line. The secondary activity may be a concentration of activity within a region. A density of peaks may be considered activity. For example, if there are 20 peaks or more in a 1 m×1 m area then that density of peaks may be considered secondary activity. The secondary activity may stay consistent from foil section to foil section. For example, as the consistent increases the secondary activity may decrease and the secondary activity may remain consistent. The secondary activity at the stock activity line may drop to about 5 percent or less, about 2 percent or less, or about 0 percent. The secondary activity may decrease from foil section to foil section. The secondary activity in a first section (i.e., the section closest to the head box) may be between about 40 percent and 1 percent, between about 30 percent and about 2 percent activity, preferably between about 15 percent and about 2.5 percent of the total activity (i.e., about 3 percent of the total activity). The secondary activity my lower from section to section. The secondary activity may remain consistent from section to section. The secondary activity may decrease by about 5 percent or less, about 2 percent or less, or about 0.5 percent or less from section to section. The secondary activity may decrease by about 30 percent or less, about 25 percent or less, or about 20 percent or less from section to section. The amount of secondary activity may be varied from grade to grade. The secondary activity may be varied by changing a primary activity line, a secondary activity line, or both. The secondary activity line may be determined by a percentage of a peak height. For example, if a peak height is 3 mm then the secondary activity line may be set at 60 percent of a peak height (i.e., 1.8 mm). The peak height may be about 30 percent or more, about 40 percent or more, about 50 percent or more, about 55 percent or more, or about 60 percent or more of a peak height (e.g., amplitude) of the activity. The secondary activity may change to tertiary activity as measurements are taken in the machine direction. For example, in the first section the secondary activity may be about 4 percent and the tertiary activity may be about 50 percent and then in the second section the secondary activity may be about 3 percent and the tertiary activity may be about 70 percent.

The tertiary activity may be any activity that falls below a threshold measurement. The tertiary activity may be laminar flow, low turbulence flow, stock that does not include peaks (i.e., amplitude), or a combination thereof. The tertiary activity may be any activity that falls below a threshold (e.g., a determination for secondary activity). The tertiary activity may increase as the stock travels towards the activity line. At the activity line all of the stock may be tertiary activity. Once the consistency reaches 3 percent or more, four percent or more, or even 5 percent or more all of the activity may become tertiary activity.

The monitoring region may be a predetermined region, a standard region, or both. The monitoring region may be a section in the cross-machine direction. The monitoring region may have a dimension in the cross-machine direction and a dimension in the machine direction so that an area is formed. A plurality of monitoring regions may exist in the cross-machine direction. A plurality of monitoring regions may be located side by side and span across the cross-machine direction. The monitoring regions may be aligned with an activity line so that spouts above a predetermined activity line can be measured in each monitoring region. The monitoring regions may span between the head box and the activity line. The monitoring regions may have a length that is equal to the length of a foil section. The monitoring regions may have a width that is equal to ⅛ or more, ¼ or more, ½ or more of a cross section of a paper machine. The monitoring regions may have a width that is equal to a width of the paper machine or less or about ¾ or less of a cross-section of a paper machine. The monitoring region may cover any standard area. An area of about 0.25 m² or more, about 0.5 m² or more, about 1 m² or more, about 2 m² or more, about 10 m² or less, or about 5 m² or less may be monitored. The monitoring regions may be in the middle of the paper machine, on an edge of the paper machine, may be from one edge to a second opposing edge, or a combination thereof. The monitoring region may monitor a height above the monitoring region (and the area). The height monitored may be about 1 cm or more, about 2 cm or more, about 5 cm or more, about 10 cm or more, about 100 cm or less, about 75 cm or less, or about 50 cm or less above an activity line. The height monitored may extend above and below an activity line. The height monitored above the activity line may be equal to a height monitored below an activity line.

The activity line may be a standard line that activity, spout heights (i.e., amplitude), or both are compared. The activity line may be located a predetermined distance above the wire, foils, or both. The activity line may be the height of stock in the absence of activity. The activity line may be the same height for all grades. The activity line may be changed for each grade. The activity line may be about 1 cm or more, about 2 cm or more, about 5 cm or more, about 10 cm or more, about 50 cm or less, about25 cm or less above the wire, the foils, or both. The activity line may be a plurality of activity lines. Each line may separate the activity into a different category. The activity lines may be a primary activity line, secondary activity line, tertiary activity line, or a combination thereof. The activity lines may measure a quantity of activity that extends above the activity line, between two activity lines, below an activity line, or a combination thereof. The activity lines may be an arbitrary line that may be moved depending on sheet formation characteristics, dry end testing requirements, wire speed, The monitoring system may monitor and/or control with a method. The method may include one or more steps performed in any order. The method may monitor the stock movement or stock activity. The stock activity may be compared to a reference stock activity or an activity line. The stock activity may be compared to a saved stock activity from a prior run of a paper grade. The stock activity may be compared to a saved stock activity when a wire is a similar worn condition. For example, if the wire is 30 days old then the stock activity is compared to a reference activity on the paper machine when the wire is 30 days old. A change between the monitored activity and the reference activity are compared. The change is compared to a predicted formula, a predicted change, or both. The method may include a step of categorizing the stock activity. The stock activity may be categorized into primary activity, secondary activity, tertiary activity, or a combination thereof. The change is used to predict the position of the components on the paper machine to lower the change. The change is compared to one or more stock movements and the stock movements after the change are predicted. If the change is reduced to zero the monitoring system may predict the impact on final properties of the paper, the formation of the paper, or both. The monitoring system may predict paper properties based upon the positions of the components on the paper machine, or the movement of the components on the paper machine (e.g., foils, head box, suction, speed, or any others discussed herein). The method may include a step of predicting paper properties. The method may include a step of comparing the predicted paper properties to a target sheet formation, and calculating a formation error. The method may include a step of comparing predicted paper properties to paper properties measured at the dry end. The monitoring system may predict paper properties based upon activity, a ratio of primary activity to secondary activity and/or tertiary activity, or both. The monitoring system may indicate where adjustment is needed so that a user may make an adjustment. The user may make adjustments from a distal location from the paper machine, from proximate to the paper machine, or both. The monitoring system, control system, or both may atomically make adjustments. The method includes a step of a user inputting a desired adjustment to one or more paper machine components (e.g., foils, head box, etc.) from a remote location, a proximate location, or both. The monitoring system may begin review at the head box and move towards the dry end as the activity changes and impacts are monitored. A new target formation or properties are calculated based upon the calculated changes. A new predicted formation is calculated based upon the change in the paper machine components. If a target formation is not achieved then the steps may be repeated one or more times until target formation is achieved. The difference between the predicted and the actual stock movement, paper machine properties, or both are calculated. The difference between the predicted and the actual may be used to correlate to a formation error. The difference between the predicted and the actual may be used to move one or more components of the paper machine. The difference between the predicted and the actual may be used to calculate a distance of movement of the foils, the position of the foils, the speed of the wire, the speed of the stock, the slice opening size, the amount of vacuum, or a combination thereof. The process may be repeated for each section of the paper machine. The process may begin at the head box, the slice opening, the first foil section, or a combination thereof. The process may monitor a paper machine with the monitoring system taught herein, and control the paper machine with the control system taught herein. The control system, controller, monitoring system, or a combination thereof may include memory. The control system, controller, monitoring system, or a combination thereof may record positions of each component of the paper machine (e.g., foil positions, machine speed, slice opening, stock jet velocity). The method includes a step of changing one or more of the components to a pre-recorded position in anticipation of a grade change, during a grade change, or at a beginning of a grade change.

FIG. 1A illustrates a perspective view of a paper machine 2 that includes a monitoring system 20 and a control system 40. The paper machine 2 includes a head box 4 that puts stock (not shown) on a wire 6 as the wire 6 continuously moves. The wire 6 travels under the headbox 4 to receive the stock and then over a plurality of foil sections 8 that remove water from the stock which creates a dry line 12 in the stock. The wire 6 ends at the couch roll 10 where the wire 6 turns and extends in a reverse direction. A monitoring system 20, monitors one or more locations between the headbox 4 and the couch roll 10. The monitoring system 20 as shown includes a plurality of lights 22, plurality of sensors 24, and one or more level devices 30 to monitor process conditions of the stock (not shown) along or across the wire 6. The monitoring system 20 includes high angle sensors 26 and low angle sensors 28. The low angle sensors 26 are located substantially level with the wire 6 and include a level device 30 that projects an activity line 74 that extends substantially parallel to the wire 6. The activity line 74 assists the monitoring device is measuring an amount of amplitude of the stock on the wire 6. Preferably, the activity line 74 assists in measuring the amplitude of the stock in a foil section 8. As shown, the low angle sensor 28 extends at an angle ($\beta$) or distance relative to the wire 6 or stock (not shown). The activity line 74 as shown extends at an angle ($\phi^-$) or distance above relative to the wire 6 or stock (not shown) although the activity line 74 may extend parallel to the wire or stock in a cross direction. The activity line 74 as shown extends at an angle ($\phi^+$) or distance below relative to a sight line of the low angle sensor 28. The high angle sensors 26 have a sight line that extends at an angle ($\alpha$) relative to the wire or stock. The control system 40 including a controller 42 is connected to the monitoring system 20 and the paper machine 2 and preferably the foil sections 8 to control movement of the individual foils (not shown) within the foil sections 8.

FIG. 1B is a top view of a low angle sensor 28, which is positioned to view parallel to the wire 6 in the cross-machine direction as stock (not shown) travels in the machine direction 14. The low angle sensor 28 includes a level device 30 that produces an activity line 74. The low angle sensor 28 measures the activity created by a foil section 8 relative to the activity line 74. The sensor 24, which as shown, is a low angle sensor 28 is in communication with a control system (not shown).

FIG. 1C is a side view of FIG. 1B along line 1C-1C so that the side profile of the stock 60 is shown. The profile looking in the cross-machine direction is shown as the stock 60 travels on the wire 6 in the machine direction 14. The sensor (not shown) measures the amplitude 68 created by the foils 9 above an activity line 74.

Figure 1D:
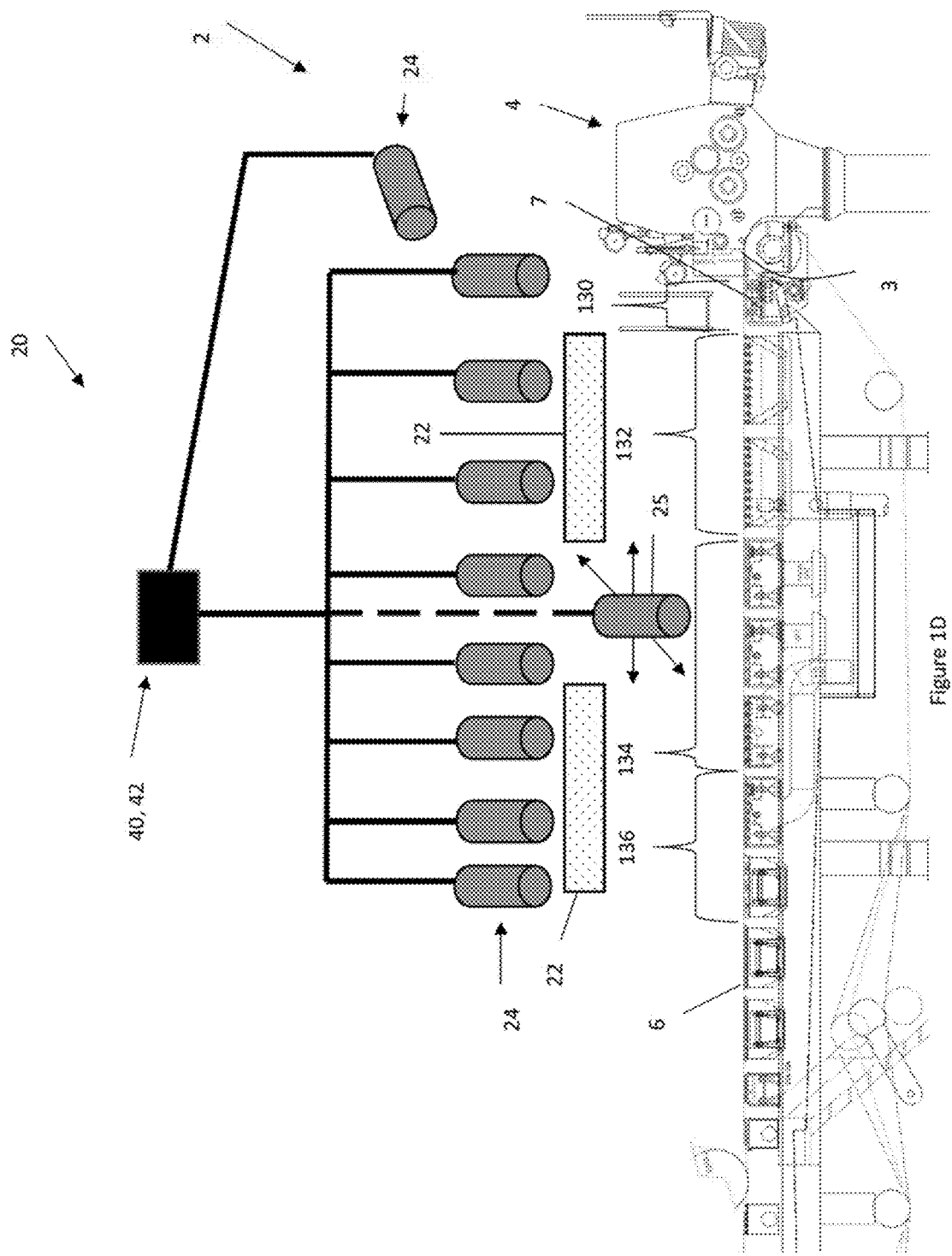
FIG. 1D is a side view of a wet end of a paper machine including a monitoring system.

FIG. 1D is a side view of a paper machine 2 with a monitoring system 20. The paper machine 2 includes a head box 4 with a slice opening 3. Stock (not shown) exits the head box 4 from the slice opening 3 and unto a wire 6 located above a forming board 7 in a forming section 130. The stock travels with the wire 6 from the forming section 130 to s132, second section 134, and the third section 136. The monitoring system 20 has a plurality of sensors 24 that monitor stock activity (not shown) as the stock travels along the paper machine 2. The monitoring system 20 includes a plurality of sensors 24, with one sensor 24 monitoring the forming section 130, two sensors 24 monitoring the first section 132, three sensors 24 monitoring the second section 134, and two sensors 24 monitoring the third section 136. The monitoring system 20 includes a movable sensor 25 that is movable in the cross-machine direction, the machine direction, or both. The monitoring system 20 also includes a sensor 24 that monitors the dry line (not shown). The monitoring system 20 further includes lights 22 that illuminate the sections of the paper machine during use of the monitoring system 20. The monitoring system 20 is connected to a control system 40 that includes one or more controllers 42 that adjust one or more elements in the forming section 130, first section 132, second section 134, and/or third section 136 to change stock activity in the respective section.

Figure 2A:
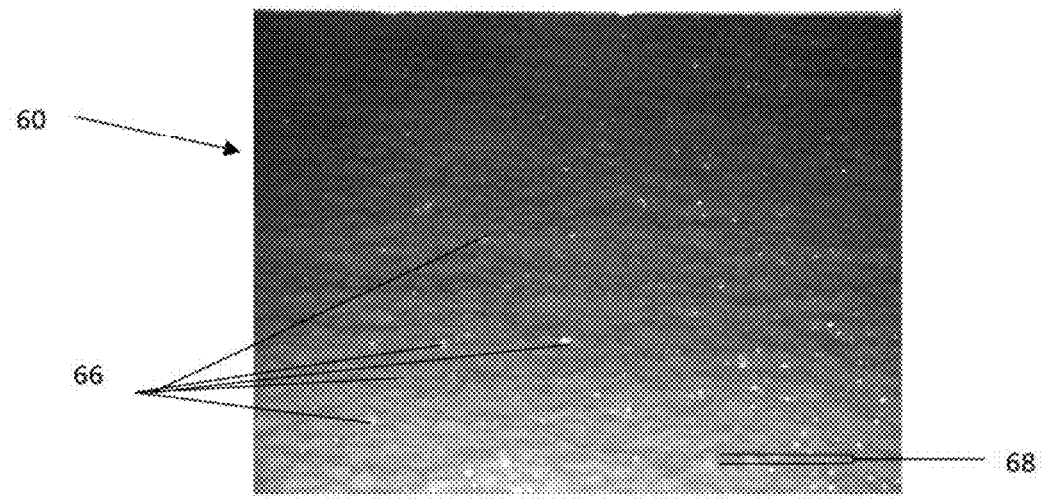
FIG. 2A is an image from a low angle sensor before a system change.

FIG. 2A is a perspective view of activity 66 (visible as white dots) of stock 60 from a low angle sensor (not shown). The stock activity 66 as shown has an amplitude 68.

Figure 2B:
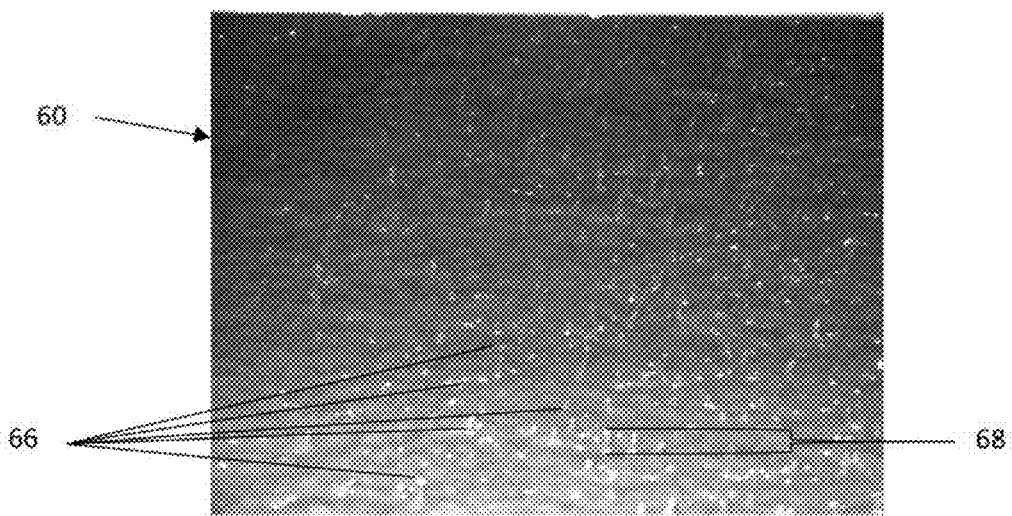
FIG. 2B is an image from a low angle sensor after a system change.

FIG. 2B illustrates activity 66 (visible as white dots and stock/fluid extending up) of stock 60 after a foil (not shown) has been adjusted from that of FIG. 2A. The amount of activity 66 is increased (by a factor of 3 or more or preferably 4 or more) and the amplitude 68 is increased (by a factor of 2 or more, 3 or more, or even 4 or more).

Figure 3A:
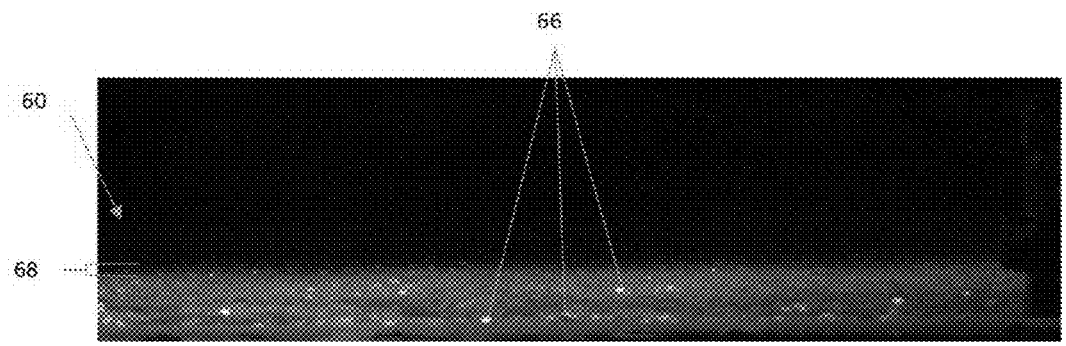
FIG. 3A is an image from a low angle sensor before a system change.

FIG. 3A illustrates a side view of stock 60 so that the amplitude 68 and activity 66 of the stock 60 is visible.

Figure 3B:
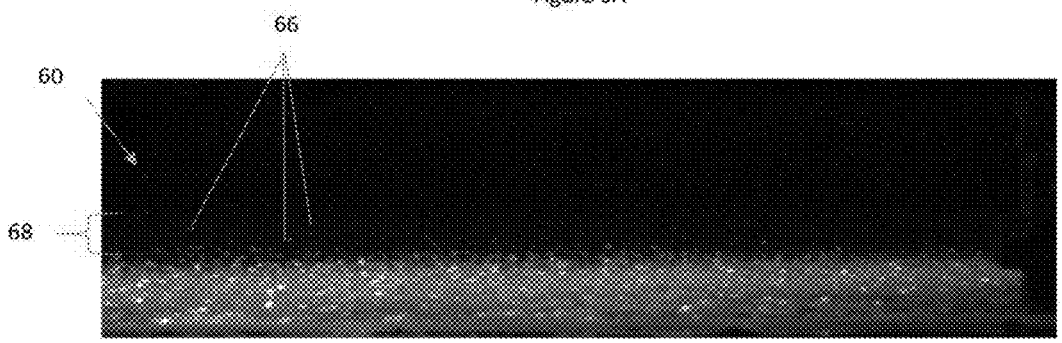
FIG. 3B is an image from a low angle sensor after a system change.

FIG. 3B illustrates a side view of stock 60 after a foil change so that amplitude 68 increases and activity 66 is increased.

Figure 4:
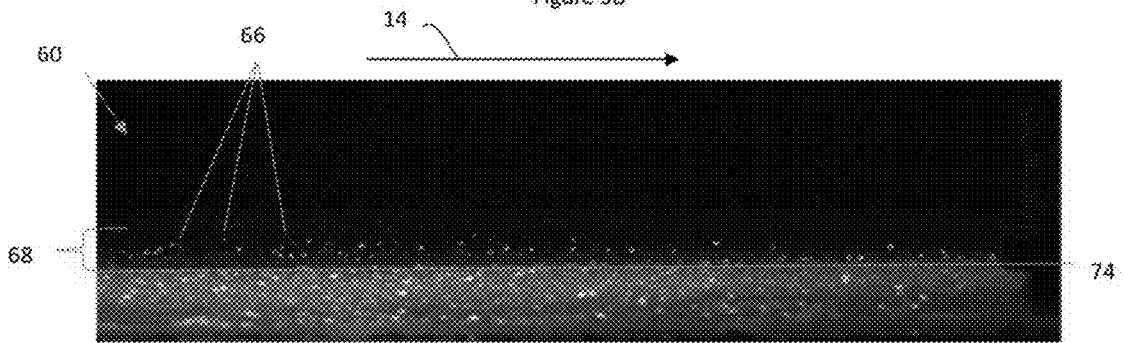
FIG. 4 is the image from 3B with an activity line indicating the amount of activity change and real-time analysis of highlighted activity over the activity line.

FIG. 4 is an analysis of FIG. 3B where the activity 66 and amplitude 68 of the stock 60 in the machine direction 14 above an activity line 74 generated by a level device (not shown), which is computer generated for analysis purposes, are highlighted for analysis.

Figure 5:
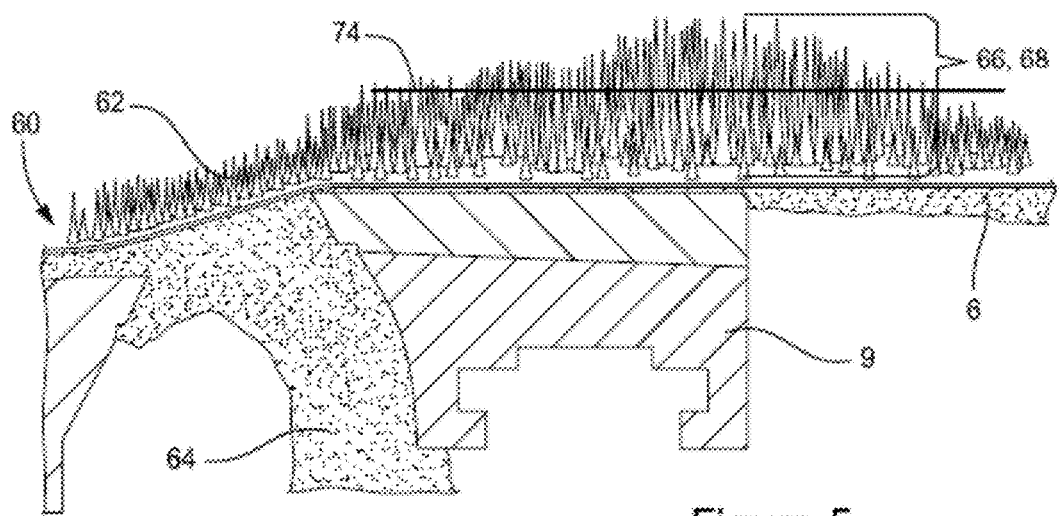
FIG. 5 is a simulation of stock activity pulsations.

FIG. 5 is a pictorial demonstration of the analysis of stock 60 as the water 64 is removed from the stock 60 by a foil 9. The stock 60 and fiber 62 move along the wire 6 and the foil 9 creates stock activity 66 (e.g., pulse density and duration) and amplitude 68 (e.g., height). The monitoring system (now shown) measures the stock activity 66 and amplitude 68 above an activity line 74.

Figure 6:
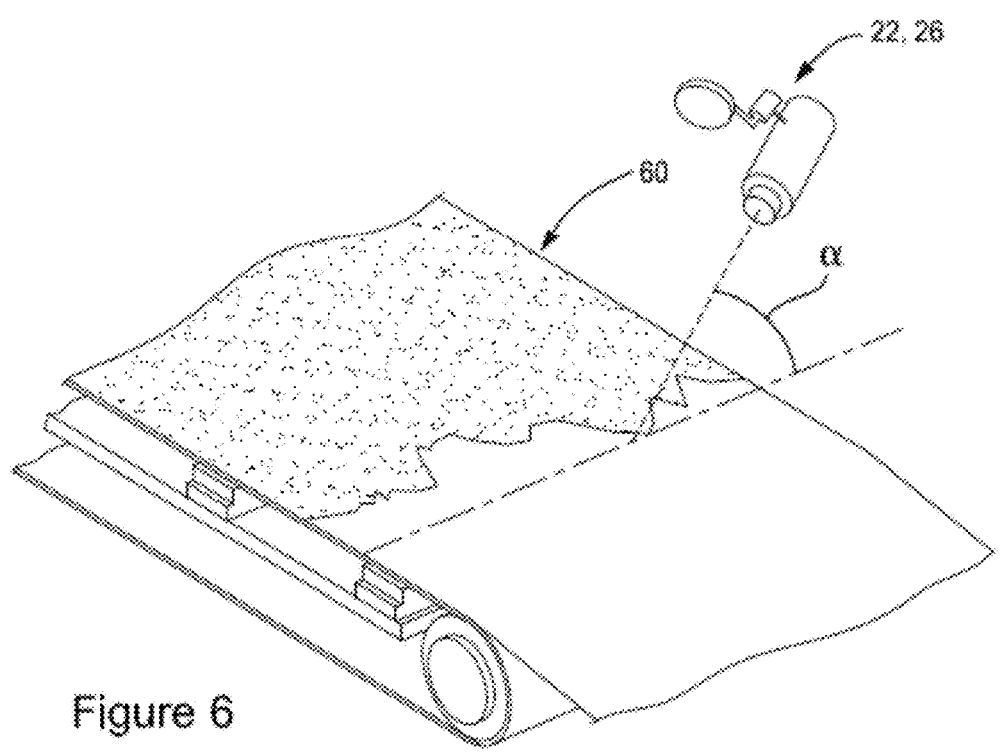
FIG. 6 illustrates a high angle sensor on the paper machine.

FIG. 6 illustrates the stock 60 and high angle sensor 26 with a light 22 that monitor at an angle (α) relative to the stock 60.

Figure 7A:
FIG. 7A is an image from a high angle sensor before a system change.

FIG. 7A illustrates a top view of stock 60 from a high angle sensor (not shown). The activity 66 (e.g., white spots) of the stock 60 is visible.

Figure 7B:
FIG. 7B is an image from a high angle sensor after a system change.

FIG. 7B illustrates a top view of stock 60 from a high angle sensor (not shown) after a foil change. The stock activity 66 is substantially increased (e.g., 2 or more times, 3 or more times, 4 or more times, or even 5 or more times) after the foil change.

Figure 8A:
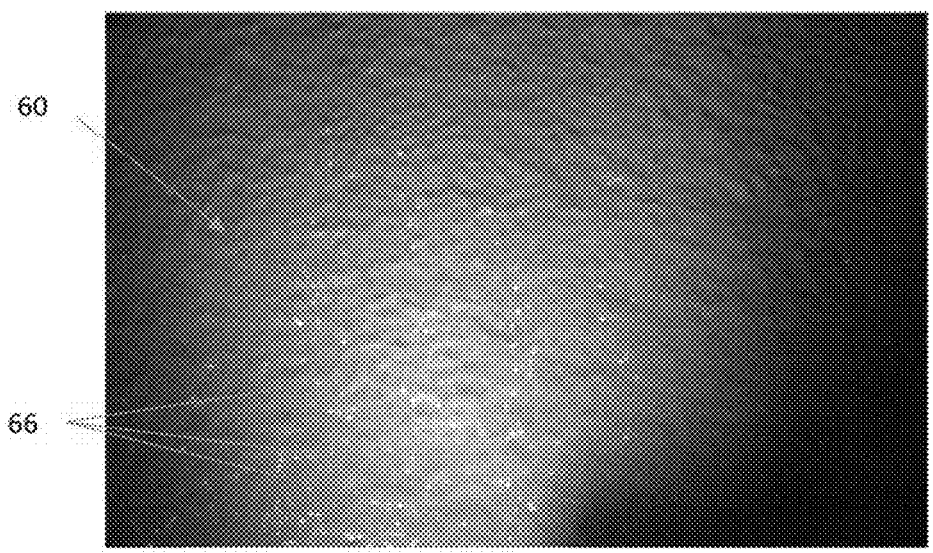
FIG. 8A is a reference image generated from a high angle sensor before engagement of a portion of the dewatering system.

FIG. 8A illustrates a top view of stock 60 from a high angle sensor (not shown) before a foil change where stock activity 66 are visible.

Figure 8B:
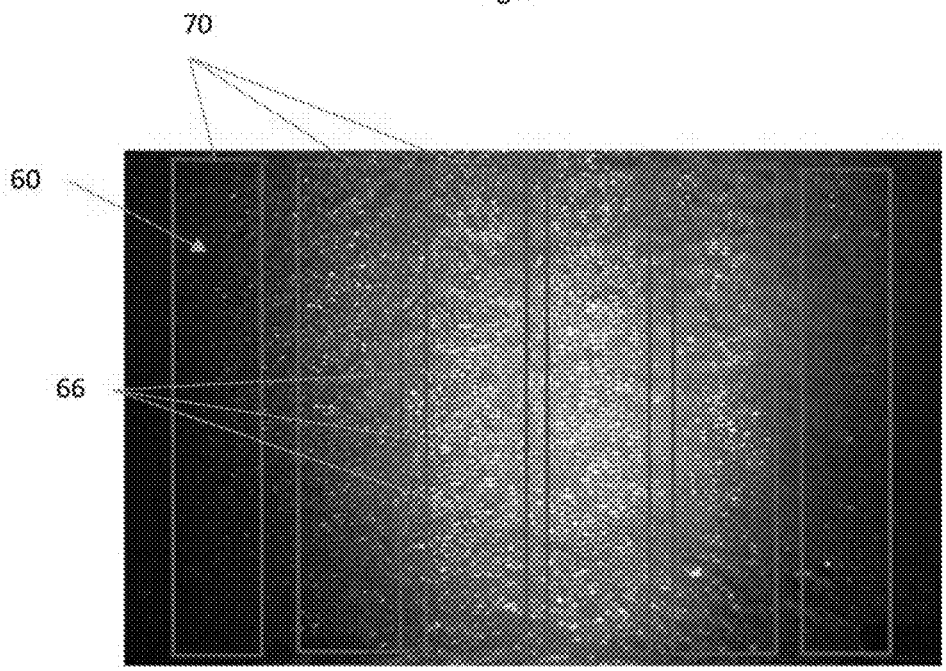
FIG. 8B is an image from a high angle sensor after a system change with the image being divided into monitoring regions.

FIG. 8B shows a change in activity 66 in the stock 60 when a foil is adjusted. Monitoring regions 70 are added to the images to correlate that amount of activity 66 relative to each foil (not shown).

Figure 9:
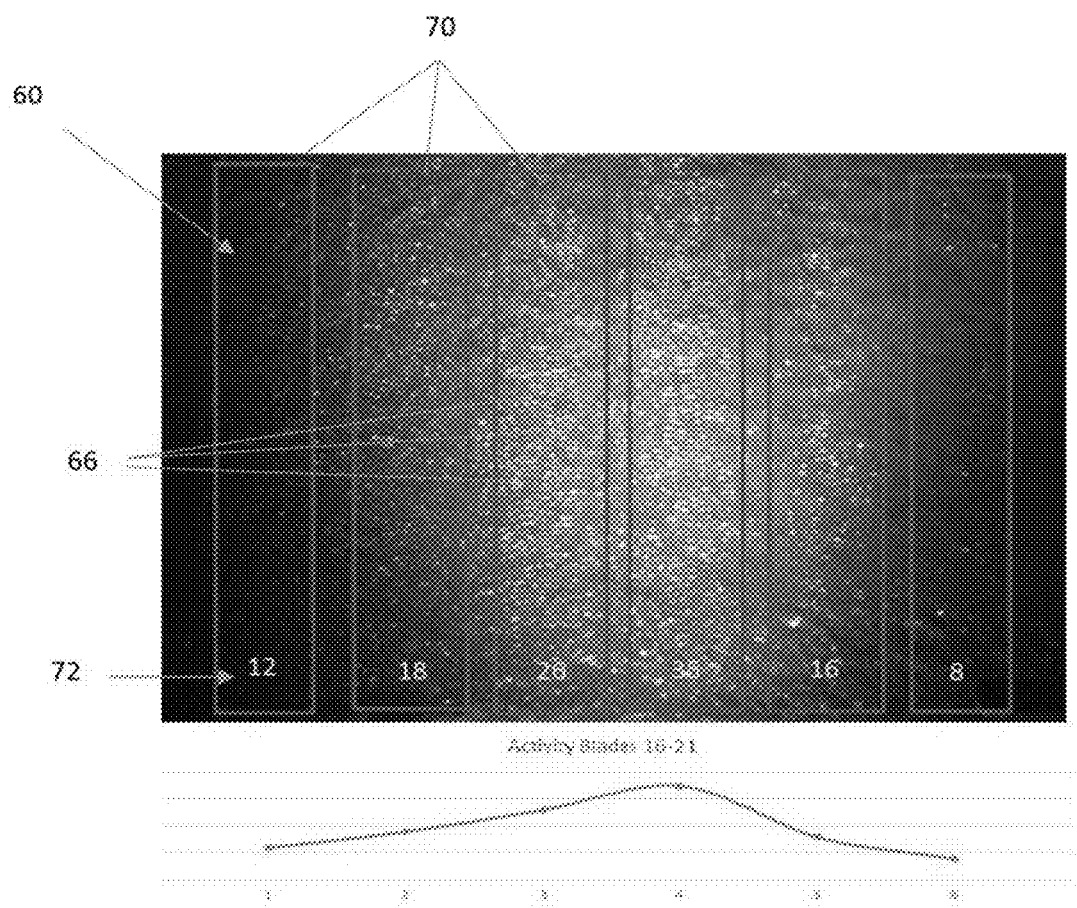
FIG. 9 illustrates an activity measurement of each monitoring region.

FIG. 9 shows an activity measurement 72 showing the amount of activity 66 of the stock 60 above the activity line (not shown) or relative to a base line measurement in each monitoring region 70.

Figure 10A:
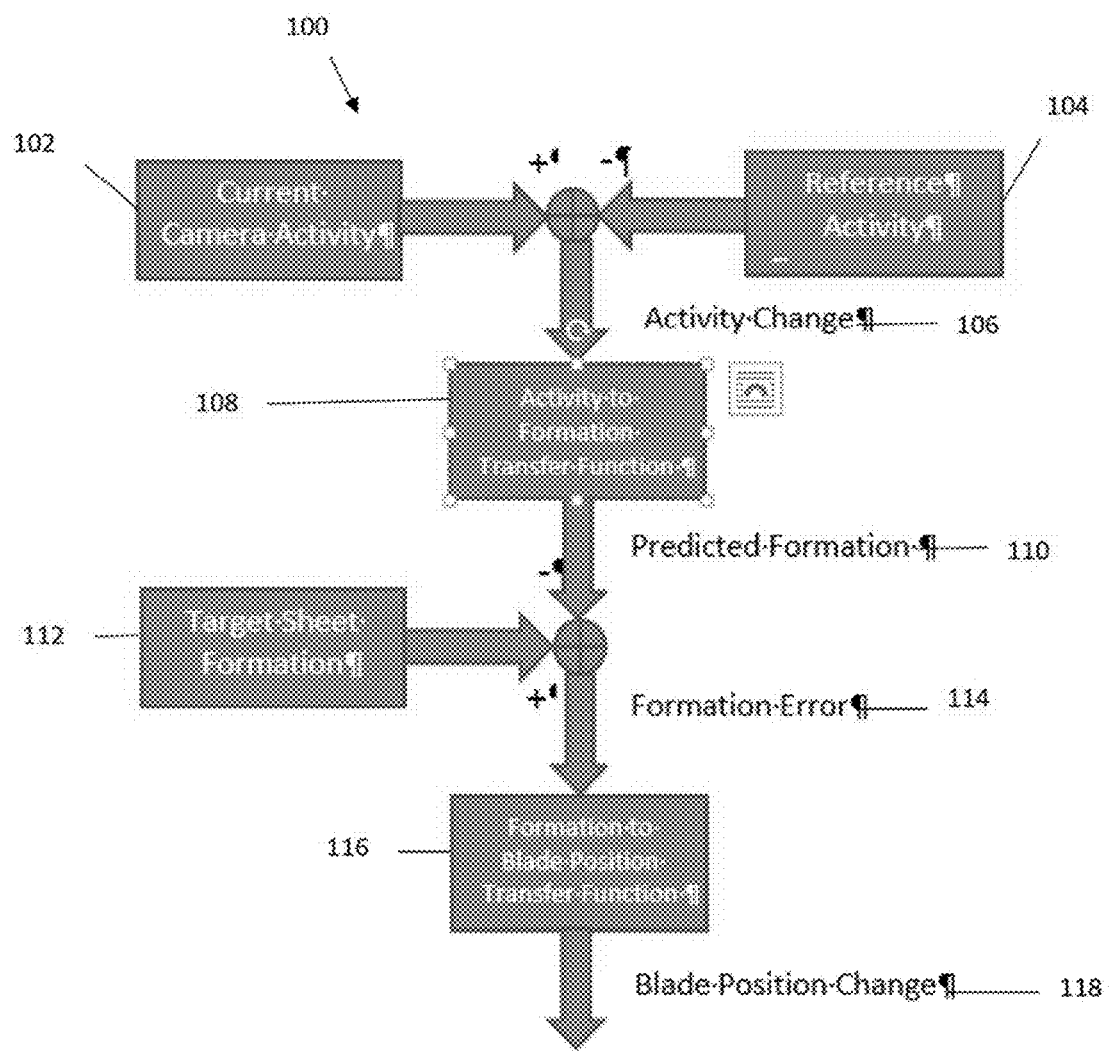
FIG. 10A illustrates a control flow chart.

FIG. 10A is a process diagram 100 where the current camera activity 102 is monitored. The monitored current camera activity 102 is compared to a reference activity 104 and an activity change 106 is calculated. The activity change 106 is monitored relative to formation to determine the impact of activity on formation and then a formation level is predicted 110. The predicted formation 110 (i.e., current formation level) is compared to a target sheet formation 112 to determine a change in formation desired or formation error 114. The formation error 114 is compared to a blade position 116 and then the blade position is changed 118 to adjust the activity and formation of the stock.

Figure 10B:
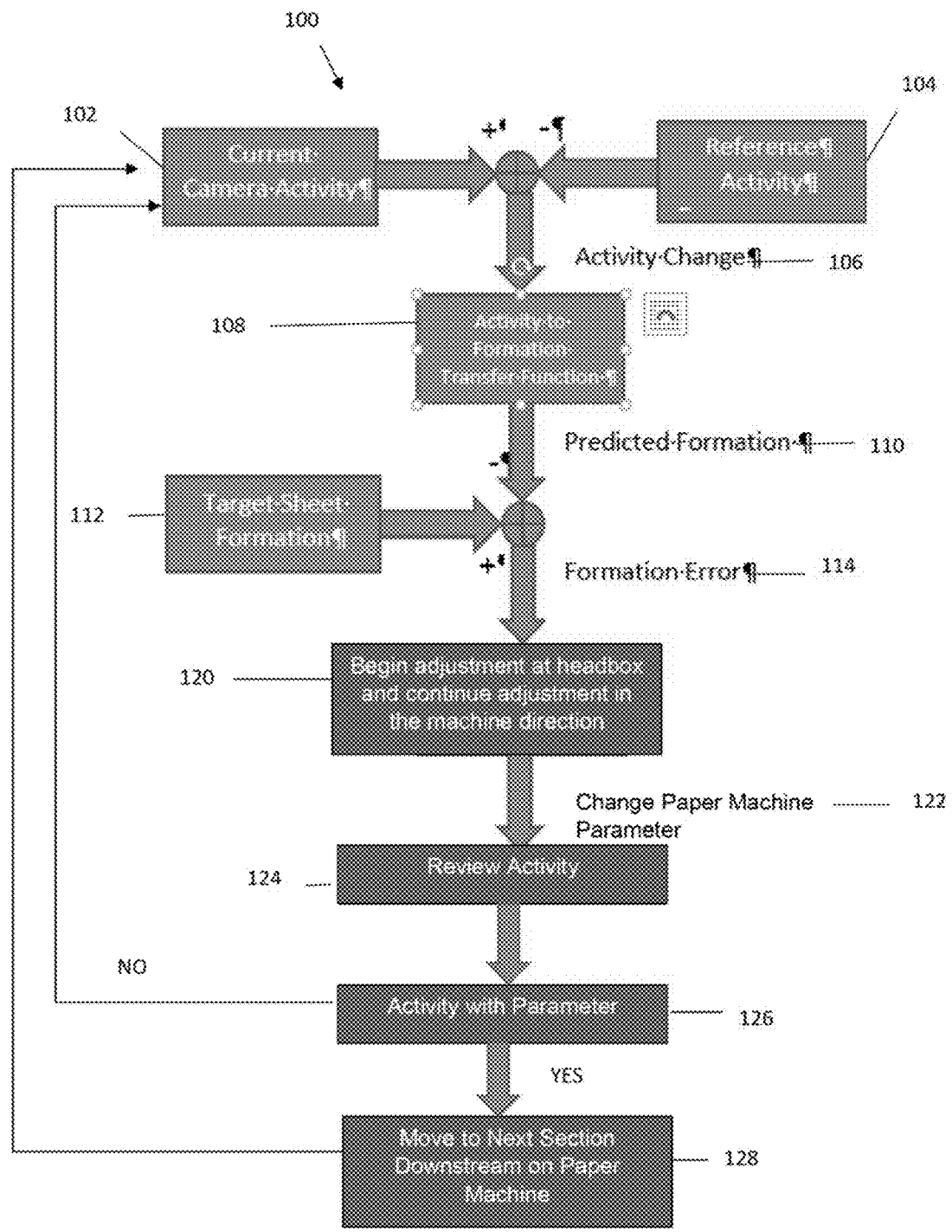
FIG. 10B illustrates a control flow chart.

FIG. 10B is a process diagram 100 where the current camera activity 102 is monitored. The monitored current camera activity 102 is compared to a reference activity 104 and an activity change 106 is calculated. The activity change 106 is monitored relative to formation to determine the impact of activity on formation and then a formation level is predicted 110. The predicted formation 110 (i.e., current formation level) is compared to a target sheet formation 112 to determine a change in formation desired or formation error 114. The formation error 114 is compared to the current paper machine settings and adjustment of paper machine parameters 120 (e.g., consistency, blade angle, slice opening, blade angle, blade height, forming board position). The paper machine parameters are changes 122 according to formation error 114. The paper machine activity is reviewed 124 for the current activity after the change. The current activity after the change is compared to a predetermined parameter of baseline activity 126. If the parameter is not met at step 126 then go back to step 102 and repeat. If the parameter is met at step 128 then proceed to the next section 128 and then begin at step 102 for the next section downstream.

Figure 11:
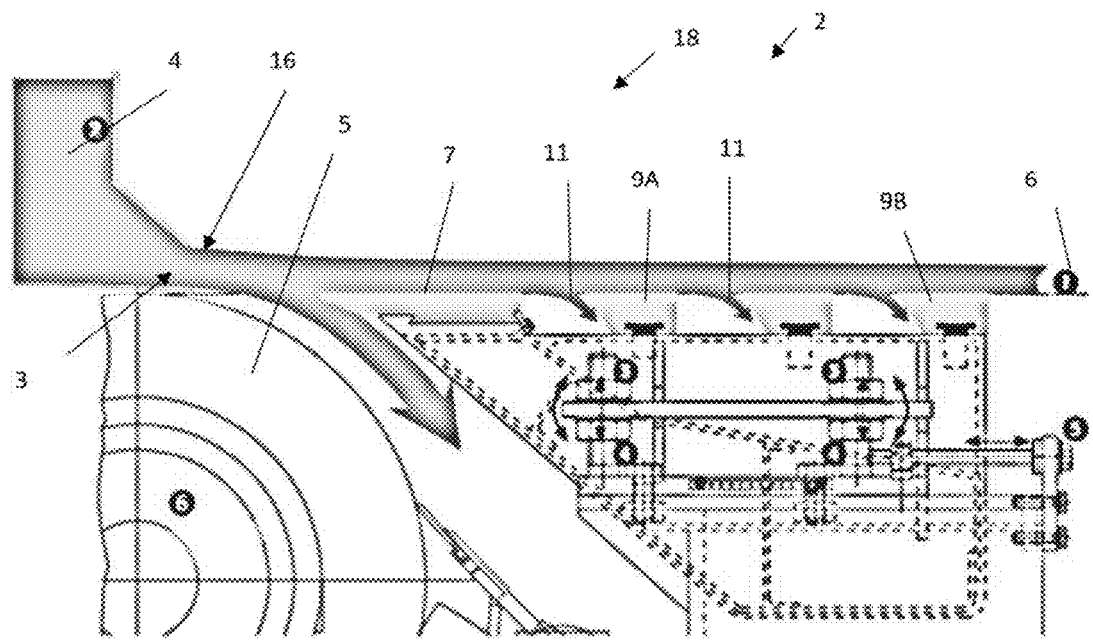
FIG. 11 illustrates a cut through and a side view of a head box and wet end of a paper machine.

FIG. 11 illustrates a wet end 18 of a paper machine 2 including a head box 4 that moves stock through a slice opening 3 forming a stock jet 16. The stock jet 16 extends towards the breast roll 5 and the wire 6 at an angle such that some water 11 is removed by passing through the wire 6 proximate to the forming board 7. The wire 6 then moves the stock across blades, which as shown are an angle adjustable foil 9A and then a height adjustable foil 9B that both remove water 11. The angle adjustable foils 9A and the height adjustable foils 9B each affect activity of the stock on the wire 6 based upon their respective position.

Figure 12:
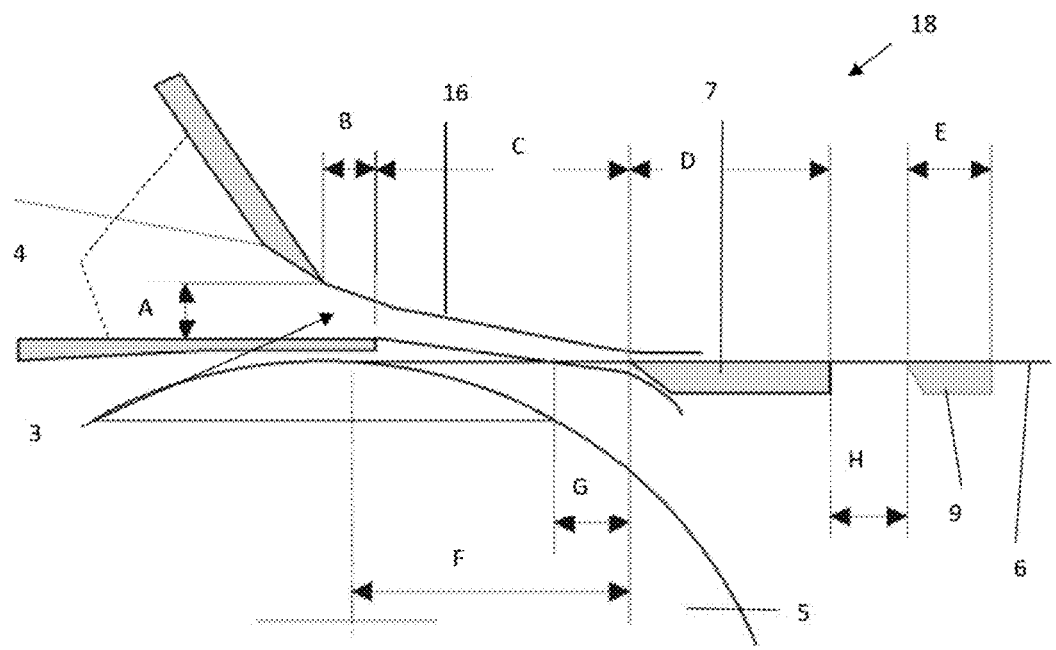
FIG. 12 is a side view of a head box and wet end of a paper machine and a relative spacing of the paper machine components.

FIG. 12 illustrates the relationship of wet end 18 pieces relative to each other. The head box 4 has a slice opening 3 with a gap (A) setting a height and a distance (B) a bottom portion of the head box 4 extends towards the forming board 7. The bottom portion of the head box 3 is located a distance (C) from the forming board 7, which has a length (D). An end of the forming board is located a distance (H) from a foil 9, which has a length (E). The angle of the stock jet 16 out of the slice opening 3 determines the length (F), which is the distance from the bottom of the head box to the point where the stock impinges with the wire 6. Distance (G) is the distance from the forming board 7 to the point where the stock impinges the wire 6.

Figure 13:
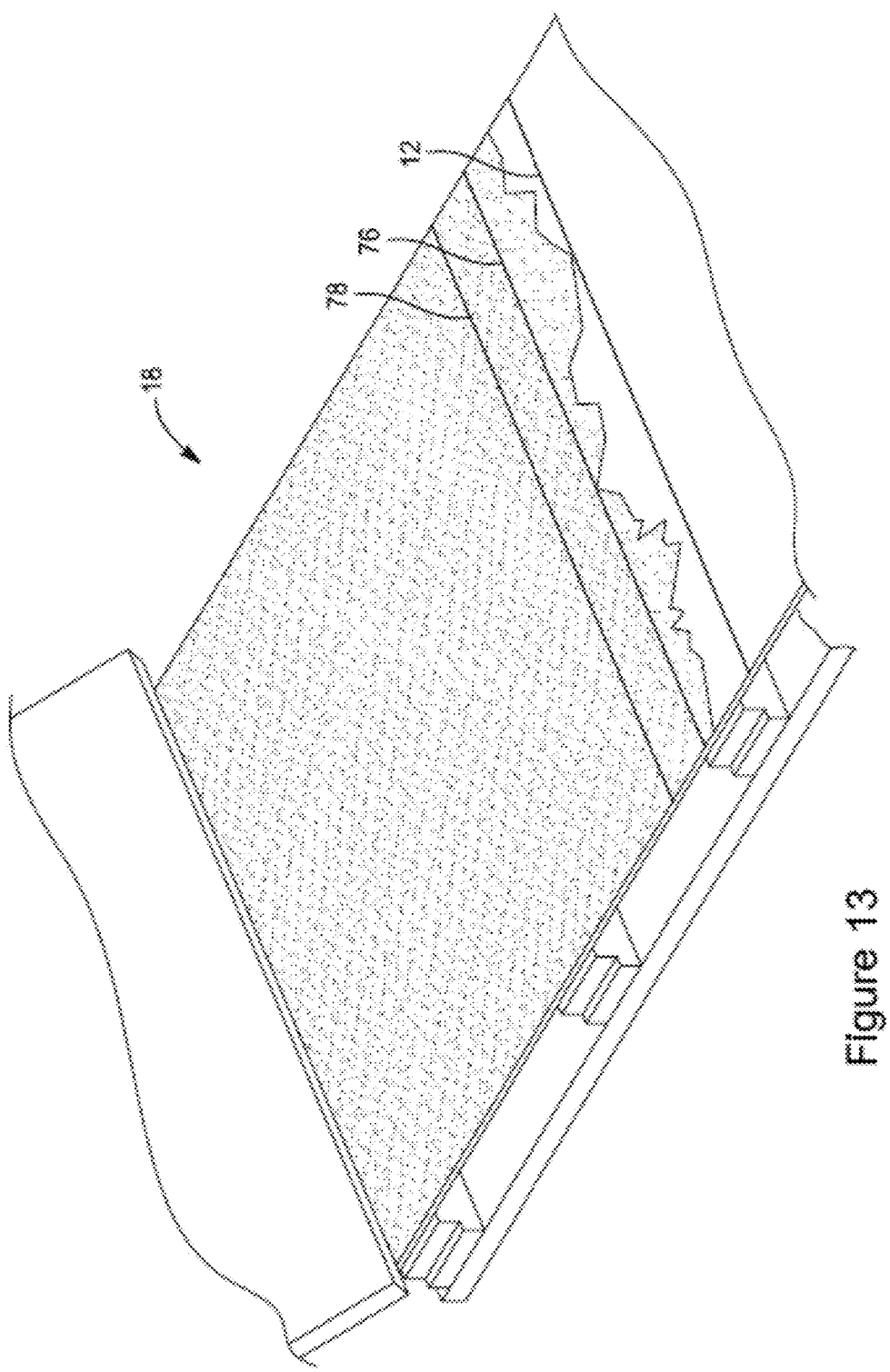
FIG. 13 is a perspective view of a dry line, wet line, and activity line.

FIG. 13 illustrates a dry line 12, wet line 76, and activity line 74 within the wet end 18.

Figure 14A:
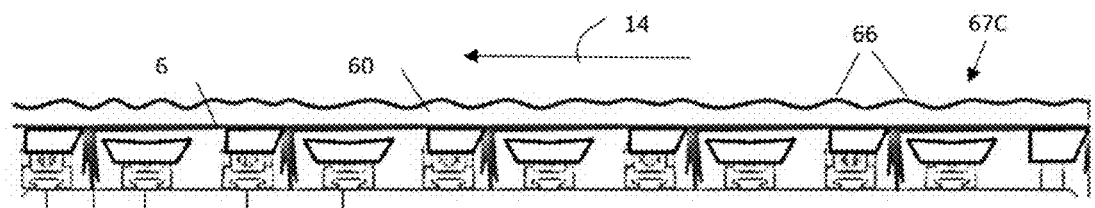
FIG. 14A illustrates a section of blades adjusted to have a low stock activity.

FIG. 14A is an example of a foil configuration setting where a majority of the stock activity 66 is tertiary activity 67C. Activity, as shown, is not imparted into the stock 60 as the stock 60 moves with the wire 6 in the machine direction 14. The angle adjustable foils 9A are in contact with the wire 6 and removing water 11 and the height adjustable foils 9B are out of contact with the wire 6.

Figure 14B:
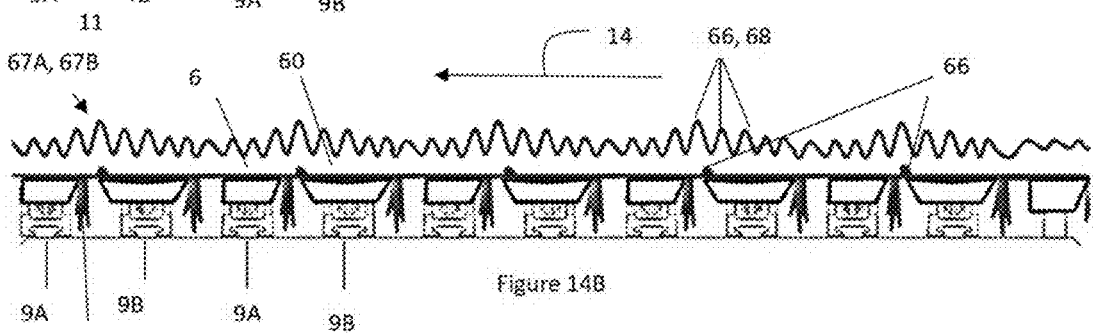
FIG. 14B illustrates a section of blades adjusted to have an intermediate stock activity.

FIG. 14B is an example of a foil configuration setting where the stock activity 66 has a combination of primary activity 67A and secondary activity 67B. Activity is imparted into the stock 60 by both the angle adjustable foils 9A and the height adjustable foils 9B as the stock 60 moves with the wire 6 in the machine direction 14. Both the angle adjustable foils 9A and the height adjustable foils 9B are in contact with the wire 6 and are removing water 11. As shown, stock activity 66 is increased on a leading side of the height adjustable foils 9B so that turbulence is generated to increase both stock activity 66 and amplitude 68.

Figure 14C:
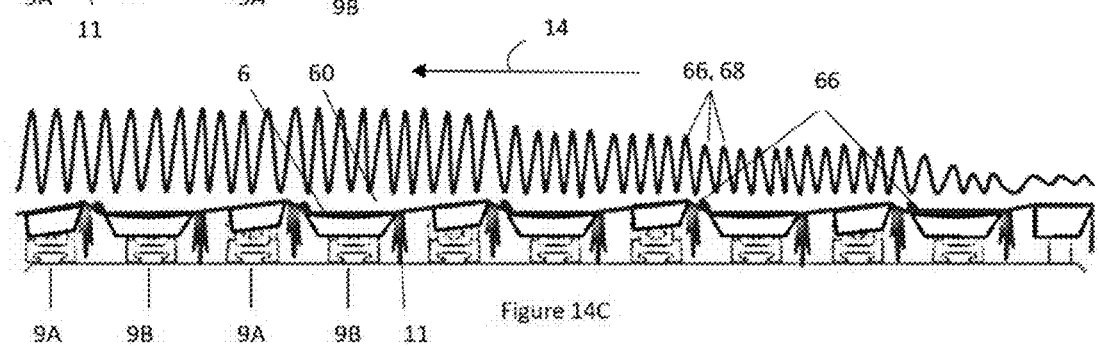
FIG. 14C illustrates a section of blades adjusted to have a high stock activity.

FIG. 14C is an example of a foil configuration setting where the stock activity 66 has a combination of primary activity 67A and secondary activity 67B. Activity is imparted into the stock 60 by both the angle adjustable foils 9A and the height adjustable foils 9B deflecting the wire 6 as the stock 60 moves with the wire 6 in the machine direction 14. As shown, turbulence as stock activity 66 is formed at a leading edge of the height adjustable blades 9B and the trailing side of the angle adjustable blades 9A. Both the angle adjustable foils 9A and the height adjustable foils 9B are in contact with the wire 6 and are removing water 11. As shown, as the wire 6 moves in the machine direction 14 the stock activity 66 increases.

Figure 14D:
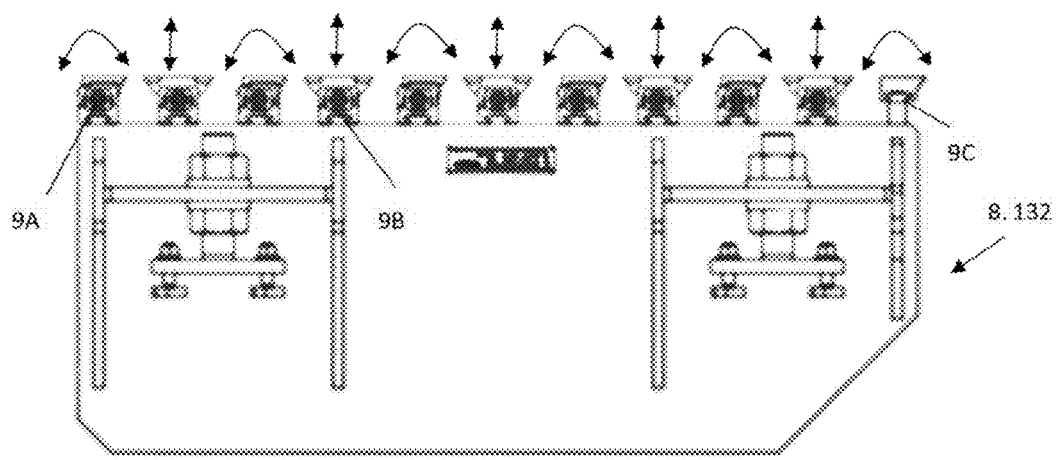
FIG. 14D is a side view of a section including both height adjustable blades and angle adjustable blades.

FIG. 14D is a side view of a foil section 8, which is a first section 132. The foil section 8 as shown includes angle adjustable foils 9A, height adjustable foils 9B, and static foils 9C.

FIG. 15A is an example of a foil configuration setting where a majority of the stock activity 66 is tertiary activity 67C. Activity, as shown, is not imparted into the stock 60 as the stock 60 moves with the wire 6 in the machine direction 14. The height adjustable foils 9B are in contact with the wire 6 at a same plane as the static foils 9C so that water 11 is removed but a low amount of activity is imparted on the wire 6.

FIG. 15B is an example of a foil configuration setting where the stock activity 66 and amplitude 68 are increased relative to the foil configuration of FIG. 15A, the foil configuration setting has a combination of primary activity 67A and secondary activity 67B. Activity is imparted into the stock 60 by the height adjustable foils 9B deflecting the wire 6 between the static foils 9C as the stock 60 moves with the wire 6 in the machine direction 14. Both the static foils 9C and the height adjustable foils 9B are in contact with the wire 6 and are removing water 11. As shown, as the wire 6 moves in the machine direction 14 the stock activity 66 increases. As shown, as the wire 6 moves in the machine direction 14 the stock activity 66 increases on a trailing side of the height adjustable foils 9B.

FIG. 15C is a side view of a foil section 8 that is a second section 134. The foil section 8 includes alternating static foils 9C and height adjustable foils 9B.

Figure 16A:
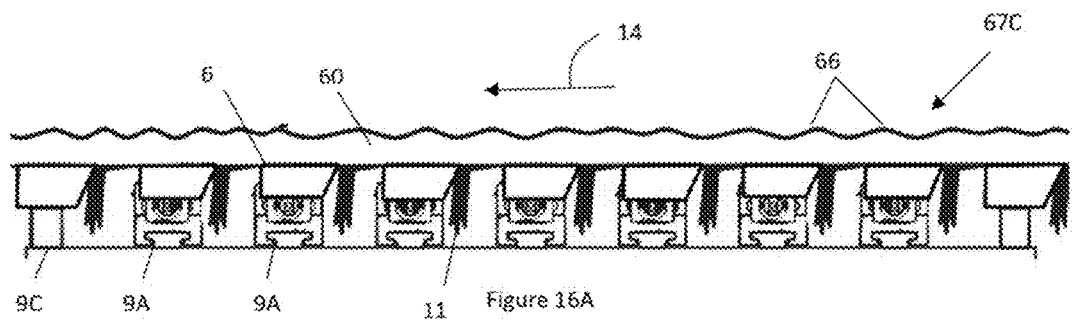
FIG. 16A illustrates a section of blades adjusted to have a low stock activity.

FIG. 16A is an example of a foil configuration setting where a majority of the stock activity 66 is tertiary activity 67C. Activity, as shown, is not imparted into the stock 60 as the stock 60 moves with the wire 6 in the machine direction 14. The angle adjustable foils 9A are in contact with the wire 6 at a same plane as the static foils 9C so that water 11 is removed but a low amount of activity is imparted on the wire 6.

Figure 16B:
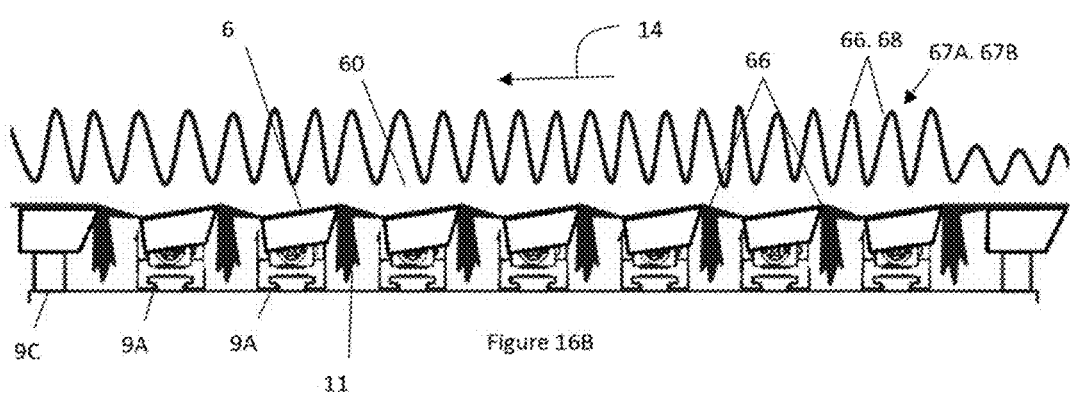
FIG. 16B illustrates a section of blades adjusted to have high stock activity.

FIG. 16B is an example of a foil configuration setting where the stock activity 66 has a combination of primary activity 67A and secondary activity 67B. Activity is imparted into the stock 60 by the angle adjustable foils 9A deflecting the wire 6 between the static foils 9C as the stock 60 moves with the wire 6 in the machine direction 14. Both the angle adjustable foils 9A and the static foils 9C are in contact with the wire 6 and are removing water 11. As shown, as the wire 6 moves in the machine direction 14 the stock activity 66 and amplitude 68 increase. Stock activity 66 is created on a trailing side of the angle adjustable foils 9A that assists in increasing amplitude 68.

Figure 16C:
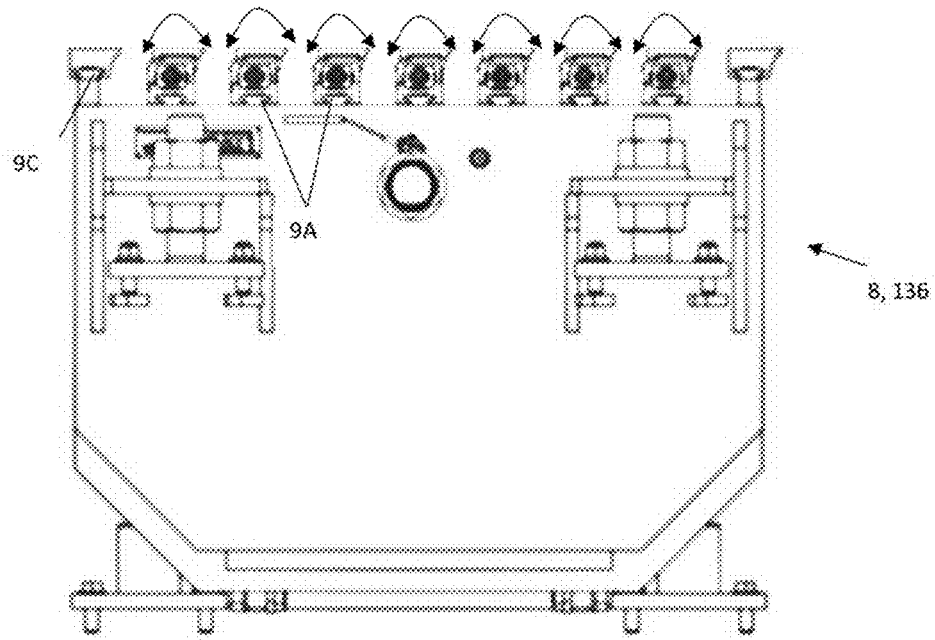
FIG. 16C is a side view of a section including both angle adjustable and static blades.

FIG. 16C is a side view of a foil section 8 that is a third section 136. The foil section 8 includes static foils 9C at the ends and angle adjustable foils 9A between the static foils 9C.

Figure 17A:
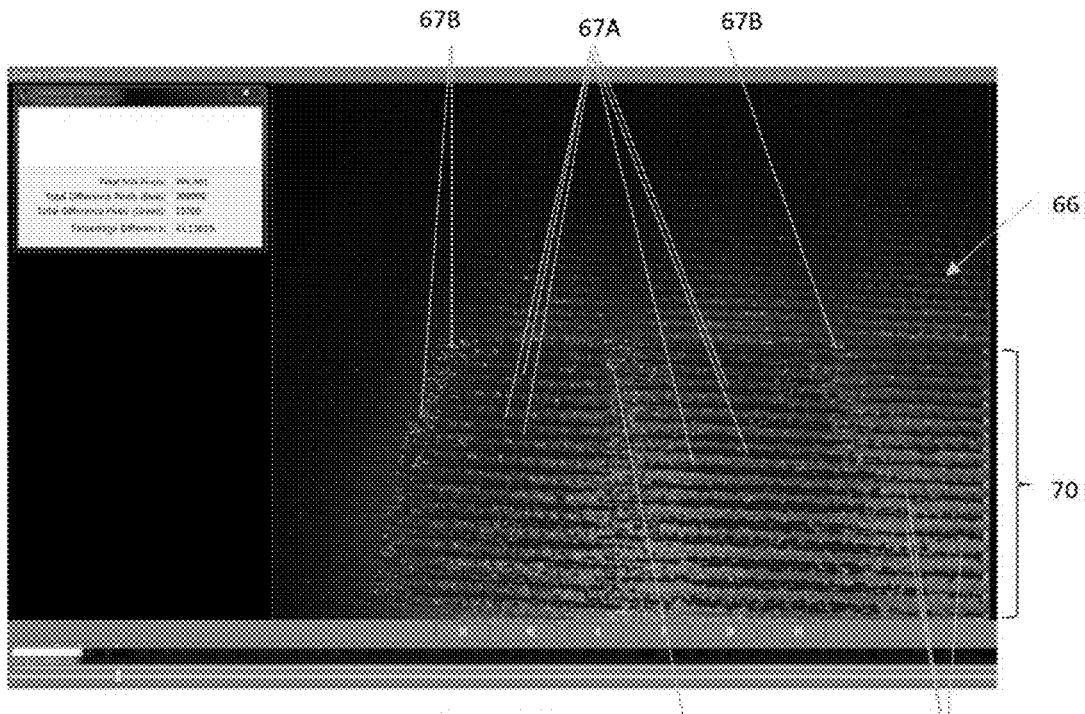
FIG. 17A is a screen shot from a camera showing stock activity.

FIG. 17A is a screen shot illustrating the categorization of stock activity 66 within a monitoring region 70. The monitoring region includes mainly primary activity 67A, some secondary activity 67B, and some intermittent tertiary activity 67C.

Figure 17B:
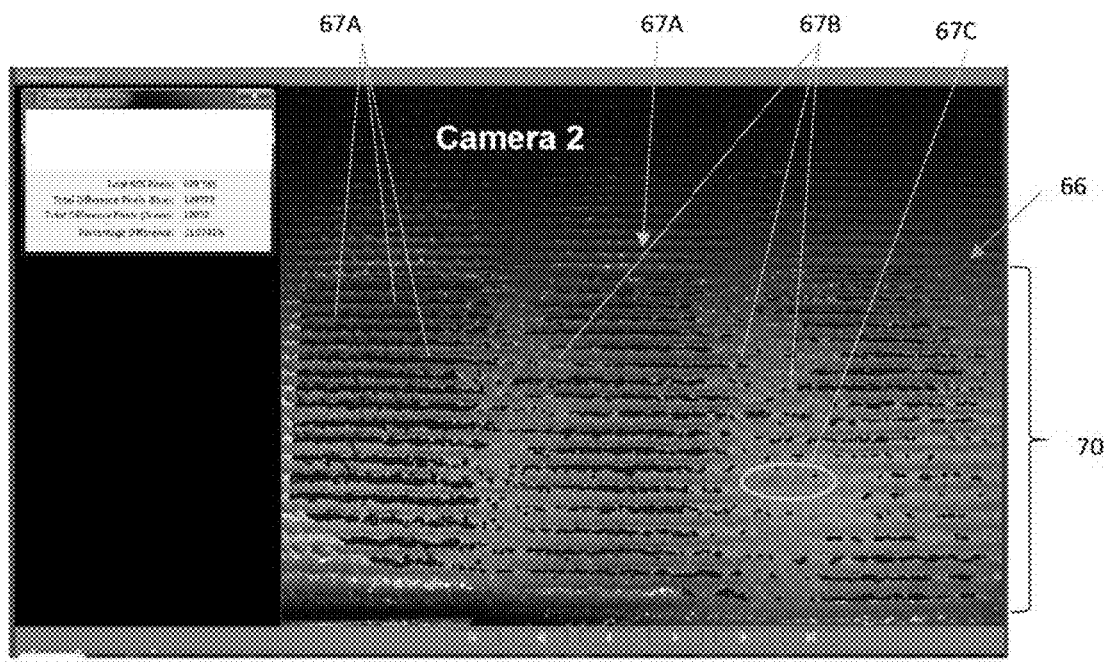
FIG. 17B is a screen shot from a camera showing stock activity.

FIG. 17B is a screen shot illustrating the categorization of stock activity 66 within a monitoring region 70. The monitoring region includes mainly primary activity 67A, some secondary activity 67B, and some intermittent tertiary activity 67C. The amount of primary activity 67A is decreases relative to the screen shot of FIG. 17A and the tertiary activity 67C is increased in FIG. 17B relative to FIG. 17A.

Figure 17C:
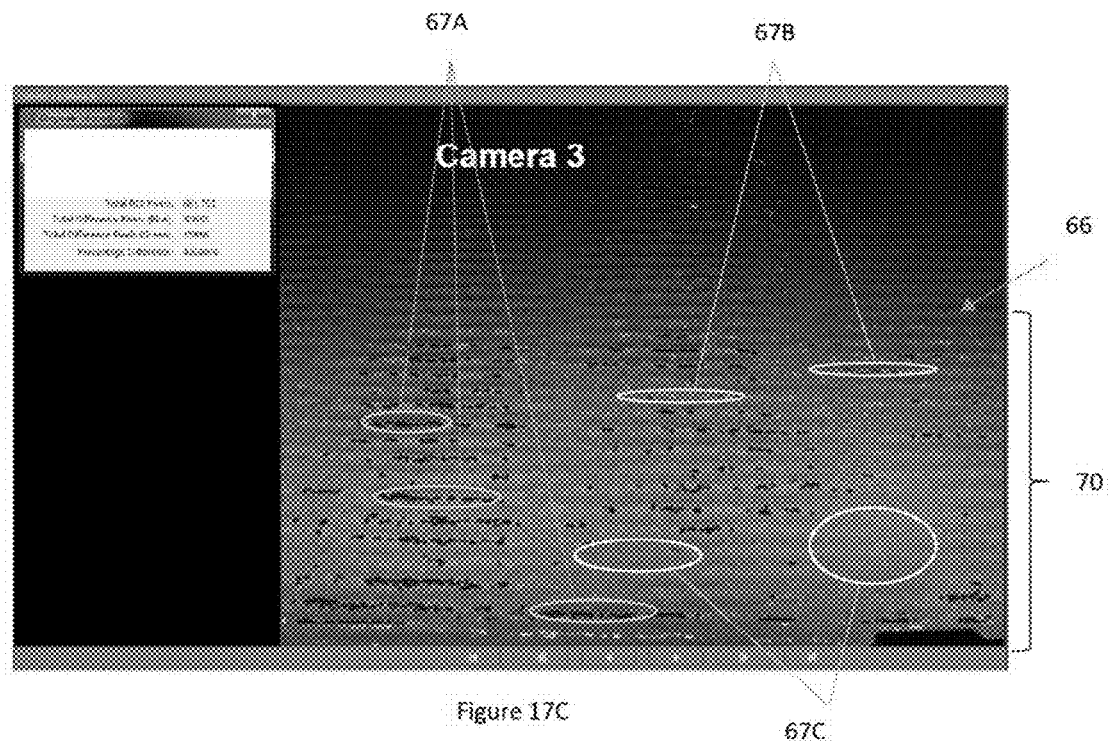
FIG. 17C is a screen shot from a camera showing stock activity.

FIG. 17C is a screen shot illustrating the categorization of stock activity 66 within a monitoring region 70. The monitoring region includes mainly primary activity 67A, some secondary activity 67B, and some intermittent tertiary activity 67C. The tertiary activity 67C is greater in FIG. 17C than in FIG. 17A and 17B, and the primary activity 67A is the lowest in FIG. 17C relative to FIG. 17A and 17B.

Figure 17D:
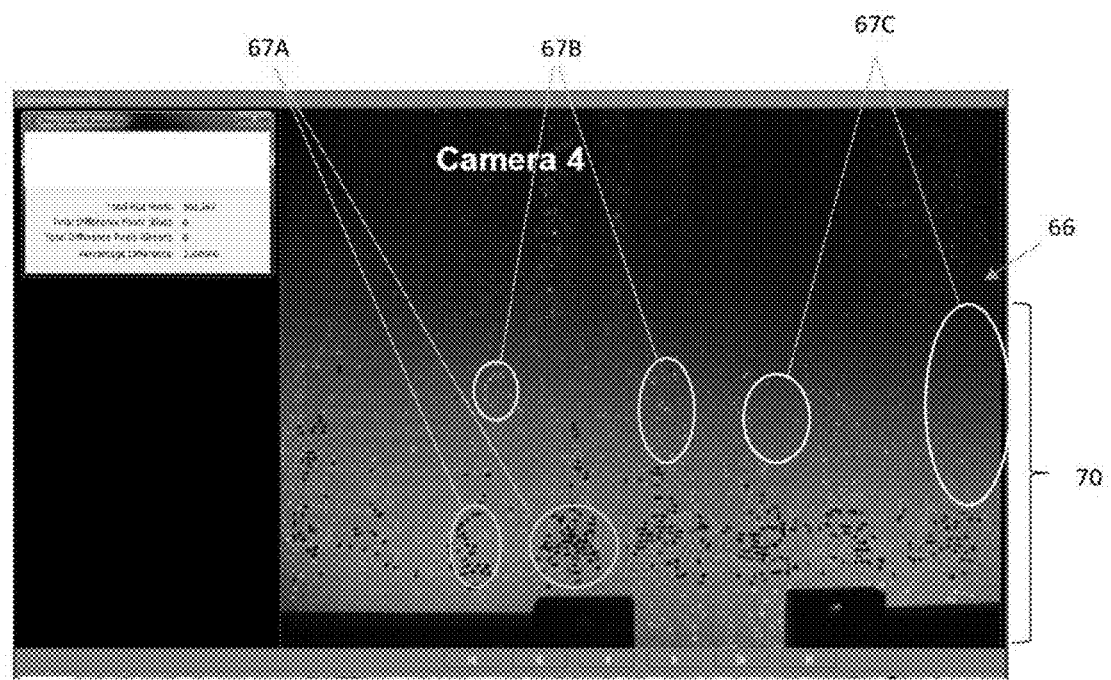
FIG. 17D is a screen shot from a camera showing stock activity.

FIG. 17D is a screen shot illustrating the categorization of stock activity 66 within a monitoring region 70. The monitoring region includes mainly primary activity 67A, some secondary activity 67B, and some intermittent tertiary activity 67C. The tertiary activity 67C is greater in FIG. 17D than in FIG. 17A, 17B, and 17C, and the primary activity 67A is the lowest in FIG. 17D relative to FIG. 17A, 17B, and 17C. FIG. 17A-17D are a progression of screen shots in the machine direction and demonstrate that as water is removed from the stock the activity level of the stock decreases.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of or even consists of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

2 Paper machine
3 Slice opening
4 Headbox
5 Breast roll
6 Wire
7 Forming Board
8 Foil sections
9 Foil
9A Angle adjustable foil
9B Height adjustable foil
9C Static Foils
10 Couch roll
11 Removed water
12 Dry Line
14 Machine Direction
16 Stock jet
18 Wet end
20 Monitoring system
22 Light
24 sensor
25 Movable sensor
26 High angle sensors
28 Low angle sensor
30 Level device
40 Control System
42 controller
60 Stock
62 Fiber
64 water
66 Stock Activity
67A Primary Activity
67B Secondary Activity
67C Tertiary Activity
68 Amplitude
70 Monitoring Region
72 Activity measurement
74 activity line
76 Wet line
78 Stock activity line
100 Process
102 Monitored activity
104 Reference activity
106 Change between 102 and 104
108 Correlate the amplitude change to impact on formation
110 Predict what formation will look like
112 Compare predicated formation to target formation
114 Difference between 110 and 112
116 Correlate how much blade change is required to remove formation error 114
118 Change blade position
120 Adjust paper machine parameter
122 Change Slice Opening, Consistency, Blade Angle, Blade Height
124 Review and move
126 Activity in Parameter
128 Move to next section and repeat steps
130 Forming section
132 First section
134 Second section
136 Third section

We claim:

1. A monitoring system comprising:
 a. one or more sensors that monitor activity of stock on a paper machine and
 b. a control system in communication with the one or more sensors and one or more foil sections within the paper machine;
 wherein the control system is configured to measures the activity of the stock and is configured to correlates the activity to formation of fibers within the stock so that an angle, a height, or both of the one or more foil sections are adjusted to change the activity of the stock; and
 wherein the one or more sensors are one or more low angle sensors that are located along a side of the paper machine and monitor the paper machine in a direction substantially parallel to a wire on the paper machine and the one or more low angle sensors measure the amplitude of the stock.

2. The monitoring system of claim 1, wherein the activity is amplitude, size, scale, duration of activity, or a combination thereof in a predetermined region relative to the one or more foil sections.

3. The monitoring system of claim 1, wherein the one or more low angle sensors are a plurality of low level sensors that are located between a head box and a couch roll of the paper machine.

4. The monitoring system of claim 3, wherein the plurality of low level sensors have at least a portion that is coplanar with the wire of the paper machine.

5. The monitoring system of claim 1, wherein the one or more sensors are one or more high angle sensors, and the one or more high angle sensors are located at an angle relative to the wire of the paper machine.

6. The monitoring system of claim 5, wherein the angle is about 90 degrees or less and about 15 degrees or more.

7. The monitoring system of claim 1, wherein the one or more sensors are ultrasound, infrared, CMOS sensor, charge-coupled device, matrix camera, area scan camera, line scan camera, microwave, a temperature sensor, nuclear, capacitance, pressure, vacuum, or a combination thereof.

8. The monitoring system of claim 1, wherein the monitoring system monitors a stock jet out of a head box, a location of a forming board, a location of the forming board relative to the head box, an angle of the stock jet, an impingement angle of the stock jet relative to the wire, a cut through, a forming shower, or a combination thereof.

9. The monitoring system of claim 1, wherein the monitoring system measures an amount of water removed from the stock before a forming board, at each foil in the one or more foil sections after the forming board, or both.

10. A monitoring system comprising:
 a. one or more sensors that monitor activity of stock on a paper machine and
 b. a control system in communication with the one or more sensors and one or more foil sections within the paper machine;

wherein the control system is configured to measures activity of the stock and is configured to correlates the activity to formation of fibers within the stock so that an angle, a height, or both of the one or more foil sections are adjusted to change the activity of the stock; and wherein the monitoring system includes a level device, and the one or more sensors that measure the activity of the stock, which is an amplitude of the stock above an activity line formed by the level device; and wherein the activity, amplitude, size, scale, duration of activity or a combination thereof of the stock in a predetermined area is a density of bright spots, a number of dimples, or both captured by the one or more sensors in the predetermined region.

11. The monitoring system of claim 10, wherein the one or more sensors are ultrasound, infrared, CMOS sensor, charge-coupled device, matrix camera, area scan camera, line scan camera, microwave, a temperature sensor, nuclear, capacitance, pressure, vacuum, or a combination thereof.

12. The monitoring system of claim 10, wherein the monitoring system monitors a stock jet out of a head box, a location of a forming board, a location of the forming board relative to the head box, an angle of the stock jet, an impingement angle of the stock jet relative to a wire, a cut through, a forming shower, or a combination thereof.

13. The monitoring system of claim 10, wherein the monitoring system measures an amount of water removed from the stock before a forming board, at each foil in the one or more foil sections after the forming board, or both.

* * * * *